United States Patent
Yamada et al.

(10) Patent No.: US 9,272,835 B2
(45) Date of Patent: Mar. 1, 2016

(54) SQUEEZE CONTAINER

(75) Inventors: Takashi Yamada, Machida (JP); Yoshinori Inagawa, Chiba (JP)

(73) Assignee: Kao Corporation, Tokyo (JP)

( * ) Notice: Subject to any disclaimer, the term of this patent is extended or adjusted under 35 U.S.C. 154(b) by 578 days.

(21) Appl. No.: 13/638,988

(22) PCT Filed: Apr. 1, 2011

(86) PCT No.: PCT/JP2011/058415
§ 371 (c)(1),
(2), (4) Date: Nov. 19, 2012

(87) PCT Pub. No.: WO2011/125933
PCT Pub. Date: Oct. 13, 2011

(65) Prior Publication Data
US 2013/0058704 A1    Mar. 7, 2013

(30) Foreign Application Priority Data
Apr. 2, 2010 (JP) .................. 2010-085707

(51) Int. Cl.
B65D 83/00 (2006.01)
B05B 9/08 (2006.01)
B05B 11/04 (2006.01)
B05B 11/00 (2006.01)

(52) U.S. Cl.
CPC .......... *B65D 83/0055* (2013.01); *B05B 9/0822* (2013.01); *B05B 11/00* (2013.01); *B05B 11/048* (2013.01); *B05B 11/0043* (2013.01)

(58) Field of Classification Search
CPC combination set(s) only.
See application file for complete search history.

(56) References Cited

U.S. PATENT DOCUMENTS

| 1,459,784 | A | | 6/1923 | Loufek |
| 4,110,058 | A | * | 8/1978 | Langle et al. ............ 417/395 |
| 4,147,278 | A | | 4/1979 | Uhlig |
| 4,473,097 | A | | 9/1984 | Knickerbocker et al. |
| 4,634,430 | A | * | 1/1987 | Polaschegg ............ 604/141 |
| 5,579,936 | A | * | 12/1996 | Costa et al. ............ 215/261 |
| 6,003,547 | A | * | 12/1999 | Tippmann, Jr. ............ 137/588 |
| 6,948,918 | B2 | * | 9/2005 | Hansen ............ 417/395 |
| 6,971,859 | B2 | * | 12/2005 | Yamamoto et al. ....... 417/395 |
| 7,461,671 | B2 | * | 12/2008 | Ehwald et al. ............ 141/244 |

(Continued)

FOREIGN PATENT DOCUMENTS

| JP | 39-006064 U | 3/1964 |
| JP | 59-46384 A | 3/1984 |

(Continued)

OTHER PUBLICATIONS

International Search Report Issued Apr. 26, 2011 in PCT/JP11/58415 Filed Apr. 1, 2011.

*Primary Examiner* — David Walczak
(74) *Attorney, Agent, or Firm* — Oblon, McClelland, Maier & Neustadt, L.L.P.

(57) ABSTRACT

A squeeze container includes a concave storage portion in which a content is stored, a sheet-shaped elastic body arranged to cover an opening portion of the storage portion, pressurization mechanism configured to swell the elastic body to the storage portion side with gas pressure, and a delivery passage which provides communication between the inside and outside of the storage portion and which delivers the content squeezed by the elastic body to the outside. The pressurization mechanism is structured to be capable of gradually swelling the elastic body by repeating squeezing with a hand and releasing thereof.

17 Claims, 26 Drawing Sheets

(56) References Cited

U.S. PATENT DOCUMENTS

| | | |
|---|---|---|
| 7,766,032 B2 | 8/2010 | Norimatsu et al. |
| 2004/0065700 A1 | 4/2004 | Milian |
| 2004/0067394 A1 | 4/2004 | Sadamoto et al. |
| 2008/0083415 A1 | 4/2008 | Umeno et al. |
| 2008/0241631 A1 | 10/2008 | Norimatsu et al. |
| 2010/0075001 A1 | 3/2010 | Succar et al. |
| 2010/0168637 A1 | 7/2010 | Casey et al. |

FOREIGN PATENT DOCUMENTS

| | | |
|---|---|---|
| JP | 60-251061 A | 12/1985 |
| JP | 64-029267 A | 1/1989 |
| JP | 7-17828 Y2 | 4/1995 |
| JP | 7-44734 U | 11/1995 |
| JP | 10-181762 A | 7/1998 |
| JP | 2000-297018 A | 10/2000 |
| JP | 2002-2757 A | 1/2002 |
| JP | 2002-114279 A | 4/2002 |
| JP | 2004-42928 | 2/2004 |
| JP | 2004 142831 | 5/2004 |
| JP | 2006 502054 | 1/2006 |
| JP | 2007-211352 A | 8/2007 |
| JP | 2008-162626 | 7/2008 |
| JP | 3153644 U | 8/2009 |
| JP | 2010 247878 | 11/2010 |
| WO | WO 99/29592 A1 | 6/1999 |
| WO | 2005 069419 | 7/2005 |
| WO | WO 2006/006378 A1 | 1/2006 |

* cited by examiner

Fig. 19

SQUEEZE CONTAINER

TECHNICAL FIELD

The present invention relates to a squeeze container.

BACKGROUND ART

There have been known various squeeze containers capable of pushing out a content with predetermined operation. For example, Patent Literature 1 discloses a squeeze-type brush-equipped container including a two-tire container body in which an inner container to store a content and an outer container to accommodate the inner container are combined as a container suitable for storing a content such as a hair dressing agent, hair dye and hair growing agent. The container disclosed in Patent Literature 1 includes a first check valve which is arranged at a delivery passage of a content and a second check valve which is arranged at a communication passage to introduce air mutually between the inner container and the outer container. Here, the content can be delivered through a brush portion by holding and compressing a torso portion of the container body.

Further, Patent Literature 2 discloses a container in which pressurization means to increase air pressure in an extruding tool body and a delivery pipe to provide communication between the inside and outside of the extruding tool body are arranged at the extruding tool body which is formed by covering a closed-end cylindrical body with a cover body. In the container disclosed in Patent Literature 2, a bag body accommodated in the extruding tool body is compressed owing to air pressure in the extruding tool body increased by the pressurization means and a liquid content in the bag body is delivered through the delivery pipe.

Further, Patent Literature 3 discloses a container which pushes out a content by swelling a balloon portion with a bellows pump as an embodiment in FIG. 14 and the like.

CITATION LIST

Patent Literature

Patent Literature 1: JP 2002-114279 A
Patent Literature 2: JP 10-181762 A
Patent Literature 3: U.S. Pat. No. 4,147,278
Patent Literature 4: JP 2000-297018 A
Patent Literature 5: JP 2002-2757 A

SUMMARY OF INVENTION

In the container described in Patent Literature 1, in accordance with decrease of the content in the inner container, the inner container becomes small and a space between the inner container and the outer container becomes large. Accordingly, when a remaining amount of the content becomes small, a delivery amount of the content becomes less even when the outer container is compressed with the same force as in a case of a large remaining amount of the content.

In the container described in Patent Literature 2, in accordance with decrease of a content in the inner bag, the inner bag becomes small and a space between the inner bag and an inner face of the extruding tool body becomes large. Accordingly, when a remaining amount of the content becomes small, a delivery amount of the content becomes less even when the pressurization means is operated in the same manner as in a case of a large remaining amount of the content.

The container described in Patent Literature 3 also has room for improvement for stably delivering a content.

In examples of the extruding tool of a content, a content in a cylinder is pushed out as a piston being pushed into the cylinder like an injector or a content is pushed out by squeezing a tube-like container. In the above, a position of the piston and an external shape of the container are largely varied in accordance with decrease of the content, it becomes difficult to stably push out an appropriate amount of a content when a remaining amount of the content becomes small.

The present invention provides a squeeze container capable of stably delivering an appropriate amount of a content even when a remaining amount of the content becomes small.

Further, as in the container of Patent Literature 1, when a squeeze container which delivers a content with squeeze deformation of the container adopts soft material as material of a section thereof to be deformed targeting to facilitate deforming of the container and the like, the container becomes more unlikely to be returned from a deformed state. Accordingly, usability is worsened such that the container is not returned from a deformed state into an original state or delivering a desired amount thereof takes time owing to that returning into an original state takes time, for example.

On the contrary, when firm material is adopted to facilitate returning from a deformed state, the container becomes hard to use owing to that the container is hard to be deformed even if being squeezed.

The present invention provides a squeeze container capable of smoothly performing operation to deliver a content as being superior in deformability due to squeezing and in restoration characteristics from a deformed state.

In the container described in Patent Literature 1, in accordance with decrease of the content in the inner container, the inner container becomes small and the space between the inner container and the outer container becomes large. Accordingly, when a remaining amount of the content becomes small, a delivery amount of the content becomes less even when the outer container is compressed with the same force as in a case of a large remaining amount of the content.

With respect to the above problem, the present applicant has studied a squeeze container including a storage portion in which a content is stored, a sheet-shaped elastic body which is arranged on the storage portion, pressurization means which swells the elastic body to the storage portion side with air pressure, a delivery passage which provides communication between the inside and outside of the storage portion and which delivers the content squeezed by the elastic body to the outside, and an air-bleeding device which discharges air swelling the elastic body to the outside, wherein the pressurization means includes a squeeze deformation portion which is deformed by squeezing with a hand and which is returned into an original state owing to releasing of the squeezing and a check valve which opens an intake passage to suck outer air at the time when the squeezing is released.

Through the study of the squeeze container, the present applicant found out a problem of decrease in operational freedom as the squeeze deformation portion being straitened owing to arranging of the air-bleeding device and the check valve. In addition, the present applicant found out a problem of lacking of a feeling of unity in design when arranging the air-bleeding device and the check valve at different positions as the both thereof being mechanisms exposed to the outside of the container.

The present invention provides a squeeze container with which squeezing operation to deliver a content can be performed in a wide range as providing high operability.

Further, according to various studies by the present applicant to have the above-studied squeeze container to be practiced, it was found out that there was a case that content delivery could not be stopped rapidly even when releasing squeezing of the squeeze deformation portion. As a result though studies for a cause thereof, the inventors fount out the cause as being momentarily continuous swelling of the elastic body owing to difference between outer air pressure and air pressure remaining in a space between a partition wall and the sheet-shaped elastic body (simply called remaining pressure in the present application) even after releasing squeezing of the squeeze deformation portion. Here, the problem due to the remaining pressure becomes further apparent when content viscosity is high.

The problem may occur with the squeeze container disclosed in Patent Literature 3, as well. The problem may be solved to some extent by arranging a check valve at a delivery passage of a content. However, it is required to set resistance force and the like of the check valve in accordance with content viscosity and the like. Accordingly, it is required to perform complicated operation to replace the container or the check valve in accordance with the content viscosity and the like.

The present invention provides a squeeze container with which delivery of a content is stopped relatively rapidly when squeezing of a squeeze deformation portion is released and a user can easily perform delivering of the content and stopping of the delivering without causing a feeling of strangeness.

Traditionally, as two-agent type hair dye, there has been known a product to be used after mixing two kinds of agents (a first agent and a second agent) just before usage thereof as keeping the agents in separate containers.

For example, there has been known two-agent type hair dye which includes a first agent containing an alkaline agent and a second agent containing hydrogen peroxide and which is used after mixing the first agent and the second agent just before usage thereof (see Patent Literature 4).

Further, as a product to be used after mixing two kinds of agents just before usage, there has been known a product to mix two kinds of agents for usage respectively filled in separate containers to be a predetermined ratio as being discharged from the respective containers. Further, there has been known a double type discharge container capable of discharging a first agent and a second agent with a single operation respectively from two containers arranged side-by-side (e.g., see Patent Literature 5).

Here, there is also a case that a user desires to freely determine a mixing ratio and amounts of two kinds of agents (a first agent and a second agent) in advance.

The present inventors studied a container capable of mixing a first agent and a second agent of two-agent hair dye at the inside thereof as sequentially filling the agents and delivering and applying the mixture to hair. However, in a case that liquid having high viscosity is filled into an aerosol container as the first agent and the first agent is filled into a container with gas pressure of the aerosol container after the second agent is filled into the container with a pump type injector or the like, a phenomenon that the first agent is upraised like a mountain-shape as penetrating a liquid level of the previously-filled second agent was observed.

When such a phenomenon as described above occurs, it is difficult to accurately acknowledge filled amounts of the second agent and/or the first agent even if the whole or a part of the container is transparent so that an amount of liquid filled to the inside is to be visible from the outside.

Accordingly, the present invention provides a method of filling liquid with which an amount of the liquid can be easily seen even in a case that liquid having high viscosity is filled by an aerosol container.

Further, the present invention provides a container in which liquid is more unlikely to be upraised like a mountain-shape even when liquid having high viscosity is filled to the inside by an aerosol container while an amount of the liquid filled to the inside can be acknowledged relatively accurately with visual observation.

Solution to Problem

According to the present invention, there is provided a squeeze container, including: a concave storage portion in which a content is stored; a sheet-shaped elastic body which is arranged to cover an opening portion of the storage portion; pressurization means which swells the elastic body to the storage portion side with gas pressure; and a delivery passage which provides communication between the inside and outside of the storage portion and which delivers the content squeezed by the elastic body to the outside (hereinafter, a first invention denotes this invention).

The present invention provides a squeeze container including a concave storage portion in which a content is stored, a sheet-shaped elastic body which is arranged on the storage portion, pressurization means which swells the elastic body to the storage portion side with gas pressure, and a delivery passage which provides communication between the inside and outside of the storage portion and which delivers the content squeezed by the elastic body to the outside. Here, the pressurization means includes a squeeze deformation portion which is deformed by squeezing with a hand and which is returned into an original state by releasing of the squeezing and is structured to be capable of swelling the elastic body by squeezing and deforming the squeeze deformation portion, and the squeeze deformation portion is formed like a curved convex face toward the outside of the container and includes a linear reinforcement portion which traverses an apex portion of the squeeze deformation portion and a linear thin-walled portion which is formed in a direction along a circumferential edge of the squeeze deformation portion (hereinafter, a second invention denotes this invention).

The present invention provides a squeeze container including a concave storage portion in which a content is stored, a sheet-shaped elastic body which is arranged on the storage portion, pressurization means which swells the elastic body to the storage portion side with air pressure, and a delivery passage which provides communication between the inside and outside of the storage portion and which delivers the content squeezed by the elastic body to the outside. Here, the pressurization means includes a squeeze deformation portion which is deformed by squeezing with a hand and which is returned into an original state by releasing of the squeezing and a check valve which opens an intake passage to suck outer air when the squeezing is released and is structured to be capable of gradually swelling the electric body by feeding air into an inflation chamber of which part is structured by the elastic body by repeating squeezing and releasing of the squeeze deformation portion, an air-bleeding device which discharges air in the inflation chamber to the outside is provided to the container, the air-bleeding device includes an elastic member, a plug member and a communication passage which provides communication between the inflation chamber and the outside of the container via a storage portion of the elastic member, the plug member closes the communication passage as being urged by the elastic member and opens the communication passage when being pressurized, and the intake passage which is opened and closed by the check valve surrounds a periphery of the air-bleeding device (hereinafter, a third invention denotes this invention).

Further, the present invention provides an intake-discharge integrated valve device including a plurality of intake holes with a check valve and a discharge passage which is surrounded by the intake holes and which is opened and closed with displacement of a plug member urged by an elastic member. Here, a storage portion of the elastic member structures a part of the discharge passage (hereinafter, a fourth invention denotes this invention).

The present invention provides a squeeze container including a storage portion in which a content is stored as having a delivery passage which provides communication between the inside and outside thereof, an inflation chamber, and pressurization means. Here, volume of the inflation chamber is increased owing to that the pressurization means fills gas into the inflation chamber and the content in the storage portion is delivered to the outside of the storage portion via the delivery passage owing to increase of the volume of the inflation chamber, at least a part of the inflation chamber is structured with an elastic body and the volume of the inflation chamber is increased with deformation of the elastic body while gas is filled into the inflation chamber by the pressurization means, and an inflation absorbing portion which decreases the volume of the inflation chamber at the time when gas-filling into the inflation chamber by the pressurization means is completed is provided to the container (hereinafter, a fifth invention denotes this invention).

Further, the present invention provides a squeeze container including a concave storage portion in which a content is stored as having an upper face opening, a sheet-shaped elastic body which is arranged to cover the whole opening, pressurization means, and a delivery passage which provides communication between the inside and outside of the storage portion. Here, the pressurization means includes a partition wall of which one face is covered with the elastic body, a squeeze deformation portion which is arranged at an opposite side of the partition wall to the elastic body and which is deformed by squeezing from a side opposite to the partition wall and which is returned into an original state by releasing of the squeezing, and a check valve which allows ventilation only toward the elastic body side from the squeeze deformation portion side, and a displacement portion which is displaced toward a side opposite to the elastic body when squeezing of the squeeze deformation portion is released is formed at the partition wall (hereinafter, a sixth invention denotes this invention).

The present invention provides a method of filling liquid to fill liquid discharged from an aerosol container into a container which includes a liquid storage portion with which an amount of filled liquid is visible from the outside, including performing to fill liquid with the aerosol container under conditions that a minute discharge passage capable of discharging air in the liquid storage portion is arranged at the liquid storage portion and that a positive pressure state in the liquid storage portion generated by the filling of the liquid continues until the filling is completed while excessive increase of pressure in the liquid storage portion is suppressed by the discharge passage (hereinafter, a seventh invention denotes this invention).

The present invention provides a container into which liquid is filled by an aerosol container, including a liquid storage portion with which an amount of the filled liquid is visible from the outside. Here, a discharge passage capable of discharging air in the liquid storage portion at the time of filling liquid is arranged at the liquid storage portion, and the discharge passage is formed to increase air pressure in the liquid storage portion owing to filling of the liquid and to maintain the positive pressure state during filling of the liquid while preventing the liquid in the liquid storage portion from leaking to the outside (hereinafter, a eighth invention denotes this invention).

According to the present invention, a container into which liquid is filled by an aerosol container includes a liquid storage portion with which an amount of the filled liquid is visible from the outside, and a discharge passage capable of discharging air in the liquid storage portion at the time of filling liquid is arranged at the liquid storage portion. In addition, the present invention also provides (1) a container in which the liquid storage portion is formed by screwing a container body and a cover body, and the discharge passage provides communication between the inside of the liquid storage portion and the outside of the container via a minute gap which is formed between the container body and the cover body by the screwing or (2) a container in which the liquid storage portion is formed by screwing a container body and a cover body, circular seal portions which are intimately contacted by screwing the container body and the cover body are provided respectively to the container body and the cover body, a concave portion which provides communication between the inside of the liquid storage portion and a space between faces of the container body and the cover body respectively having a screwing convex stripe is formed at a part of the circular seal portion of the container body and/or the circular seal portion of the cover body, and a part of the discharge passage is formed with the concave portion.

BRIEF DESCRIPTION OF DRAWINGS

FIG. 19 is an enlarged sectional view at line IV-IV of FIG. 18.

DESCRIPTION OF EMBODIMENTS

In the following, the present invention will be described based on preferable embodiments with reference to the drawings.

First, a first invention will be described based on preferable embodiments thereof.

Figure 2:
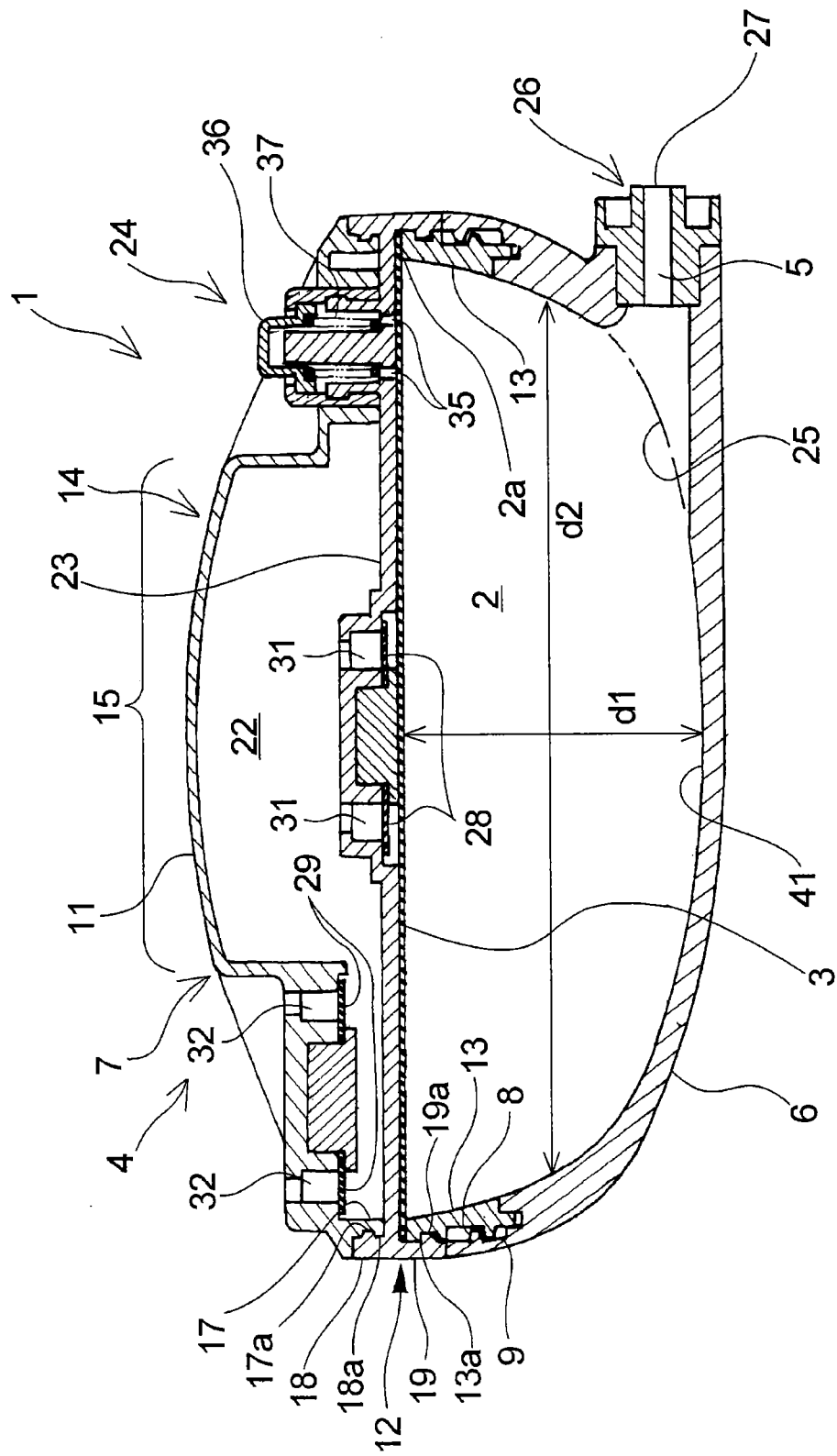
FIG. 2 is an enlarged sectional view at line II-II of FIG. 1.

As illustrated in FIG. 2, a squeeze container 1 of an embodiment (first embodiment) of the first invention includes a concave storage portion 2 in which a content is stored, a sheet-shaped elastic body 3 which is arranged on the storage portion 2, pressurization means 4 which swells the elastic body 3 to the storage portion 2 side with air pressure (gas pressure), and a delivery passage 5 which provides communication between the inside and outside of the storage portion 2 and which delivers the content squeezed by the elastic body 3 to the outside. The storage portion 2 is concaved, more specifically, concaved to be a hemispherical or partially-spherical shape. The storage portion 2 has an approximately-circular opening portion 2a at an upper face thereof. The sheet-shaped elastic body 3 is arranged to cover the whole opening portion 2a of the storage portion 2. In the container 1 of the present embodiment, gas to swell the elastic body is air (mixture gas including oxygen and nitrogen). Here, it is also possible to adopt gas other than air as the gas in the present invention. Further, the concave storage portion of the present invention may have larger sectional area at the inside thereof than area at the opening portion. Further, as in the squeeze container 1 of the present embodiment, it is preferable that the concave storage portion has an approximately-circular opening portion and a curved concave bottom face and that a depth d1 of the storage portion is smaller than a diameter d2 of the storage portion at a center part of the storage portion in the depth direction.

Figure 1:
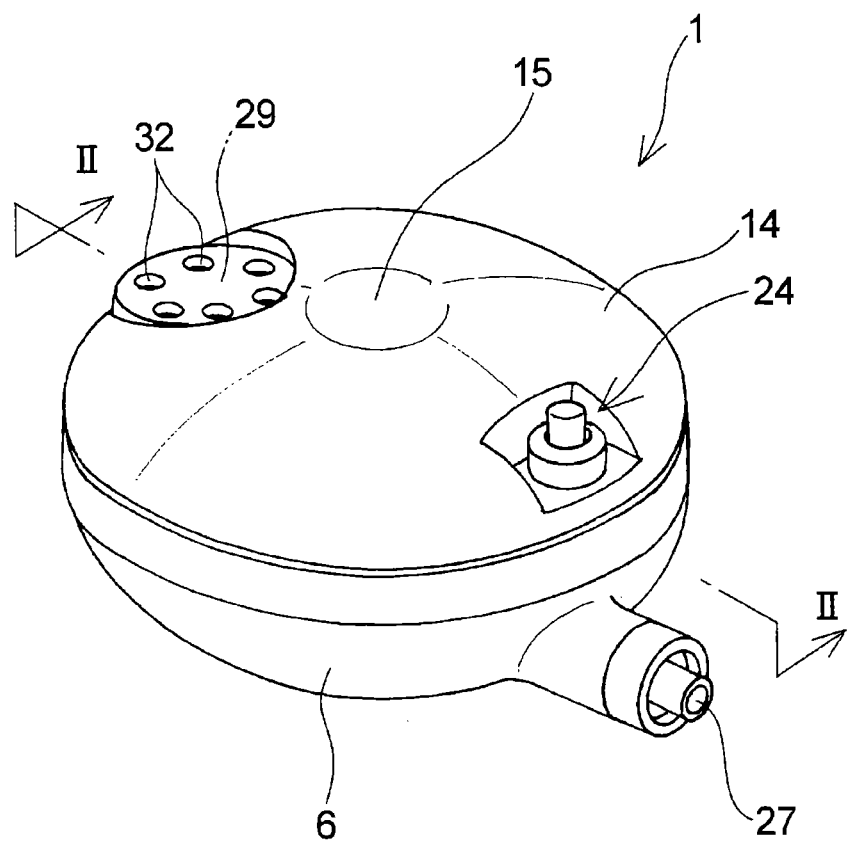
FIG. 1 is a perspective view illustrating a first embodiment of a squeeze container of the present invention (first invention).

As illustrated in FIG. 1, the squeeze container 1 roughly has a shape like a flat ellipsoidal body, so that content squeeze operation can be performed by one hand while holding with the one hand.

The squeeze container 1 includes a container body 6 which has a curved concave inner face and a cover body 7 which is attached to the container body 6 in a detachably attachable manner. The container body 6 includes a screwing convex stripe portion 8 at an inner circumferential face at an upper end part thereof and the cover body 7 includes a screwing convex stripe 9 at an outer circumferential face at a lower end part thereof. The container body 6 and the cover body 7 are screwed via the screwing convex stripe portion 8 and the screwing convex stripe 9 as being detachably attachable.

The cover body 7 includes a top face portion forming member 11, a partition wall forming member 12, the sheet-shaped elastic body 3 and an elastic body fixing member 13.

The top face portion forming member 11 forms a curved convex top face portion 14 which is convexed toward the outside of the squeeze container 1. The whole or a part of the top face portion 14 forms a squeeze deformation portion 15 which is easily deformed by squeezing with a hand and which is returned into an original state by releasing of the squeezing. Similarly to the top face portion 14, the squeeze deformation portion 15 also has a shape like a curved convex shape.

A cylindrical connection portion 17 is vertically arranged at a peripheral part of the top face portion forming member 11 in a direction opposite to a swelling direction of a curved convex face of the squeeze deformation portion 15. A pair of cylindrical connection portions 18, 19 extended vertically is arranged at a peripheral part of the partition wall forming member 12. The top face portion forming member 11 and the partition wall forming member 12 are integrated as being air-tightly connected by screwing the cylindrical connection portion 17 of the top face portion forming member 11 and the cylindrical connection portion 18 extended upwardly at the peripheral part of the partition wall forming member 12 via screwing convex stripes 17a, 18a which are arranged respectively thereto. Further, owing to the connection described above, an air chamber (pressurization chamber) 22 is formed between the top face portion forming member 11 and the partition wall forming member 12.

Figure 3:
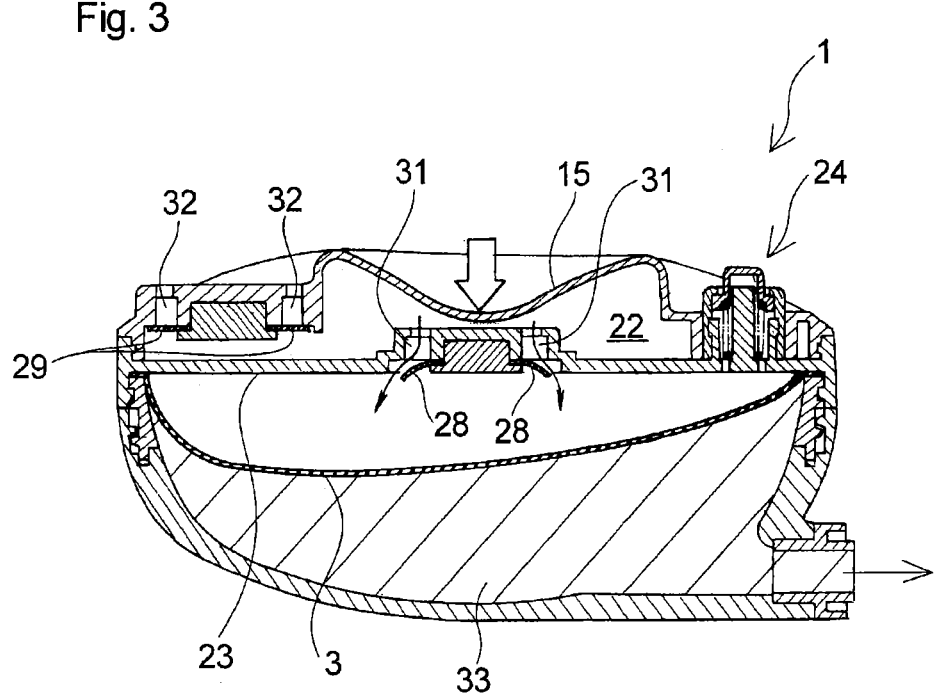
FIG. 3 is a sectional view illustrating a squeeze-deformed state of a squeeze deformation portion of the squeeze container of FIG. 1.

The partition wall forming member 12 forms a plane-shaped partition wall 23 which is circular in plane view between the air chamber 22 and the sheet-shaped elastic body 3. As illustrated in FIG. 3, there is little deformation at the partition wall 23 even when the squeeze deformation portion 15 is deformed by being squeezed with a hand.

The sheet-shaped elastic body 3 is arranged along the partition wall 23 as being closed to the partition wall 23. The sheet-shaped elastic body 3 is fixed as a peripheral part thereof being sandwiched at a space between the partition wall forming member 12 and the elastic body fixing member 13. The sheet-shaped elastic body 3 is not fixed to the partition wall forming member 12 other than the peripheral part. Accordingly, as illustrated in FIG. 3, the sheet-shaped elastic body 3 can be swelled to the storage portion 2 side with pressure (air pressure) of air fed by the pressurization means 4.

The partition wall forming member 12 and the elastic body fixing member 13 are integrated by screwing the elastic body fixing member 13 and the cylindrical connection portion 19 extended downwardly at the peripheral part of the partition wall forming member 12 via the screwing convex stripes 19a, 13a.

Here, as illustrated in FIG. 2, the sheet-shaped elastic member 3 is plane-shaped as being approximately in parallel to the flat-plate-shaped partition wall 23 in an initial state.

The elastic body fixing member 13 is cylindrical and an inner circumferential face thereof forms a curved concave face which is continued to the curved concave inner face of the container body 6. The curved concave inner face of the concave storage portion 2 is formed with the inner circumferential face of the elastic body fixing member 13 and the curved concave inner face of the container body 6. An opening portion 25 of the delivery passage 5 at the storage portion 2 side is opened into a circular or oval shape at a part of the curved concave inner face of the storage portion 2, more specifically, at a part positioning right below an air-bleeding device 24 which is described later. A nozzle member 26 is fixed to the delivery passage 5 in a detachably attachable manner. An opening portion 27 of the delivery passage 5 at the outer side is formed at the nozzle member 26. Owing to replacement thereof, it is possible to replace the nozzle member 26 with a nozzle member being different in length or diameter of a passage communicated to the opening portion 27, dimensions of the opening portion 27, or the like, or with a brush-equipped nozzle member having a brush at a periphery thereof, or the like.

The pressurization means 4 is means to swell the sheet-shaped elastic member 3 to the storage portion 2 side with air pressure. The pressurization means 4 of the squeeze container 1 of the present embodiment includes a first check valve 28 and a second check valve 29 as well as the squeeze deformation portion 15, the air chamber 22 and the partition wall 23 which are described above.

Figure 4:
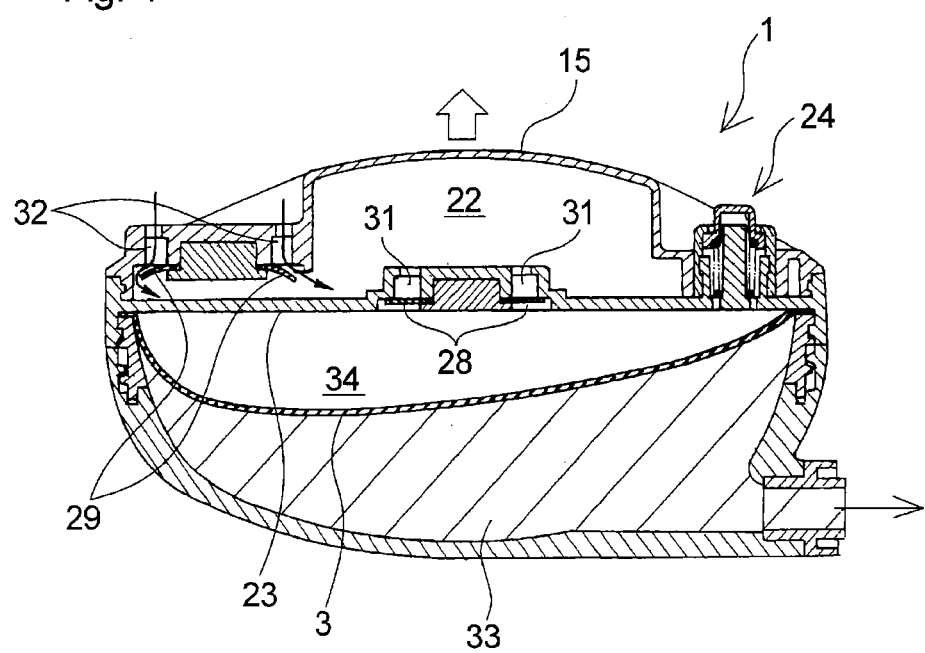
FIG. 4 is a sectional view illustrating a state that the squeeze deformation portion of the squeeze container of FIG. 1 is returned from a deformed state into an original state.

The first check valve 28 is arranged at a communication passage 31 which is formed at the partition wall 23 and feeds air in the air chamber 22 toward the elastic body 3 as opening the communication passage 31 when the squeeze deformation portion 15 is deformed as being squeezed with a hand as illustrated in FIG. 3. On the other hand, when the squeezing of the squeeze deformation portion 15 is released as illustrated in FIG. 4, the communication passage 31 is closed by the first check valve 28 and the air swelling the elastic body 3 is prevented from being regurgitated to the air chamber 22 accordingly.

The second check valve 29 is arranged at an intake passage 32 which is formed at the top face portion 14 and closes the intake passage 32 when the squeeze deformation portion 15 is deformed as being squeezed with a hand as illustrated in FIG. 3. On the other hand, when the squeezing is released after squeezing the squeeze deformation portion 15 as illustrated in FIG. 4, the squeeze deformation portion 15 is returned into an original state owing to restoration characteristics thereof. Then, the second check valve 29 opens the intake passage 32 and air outside the squeeze container 1 inflows into the air chamber 22.

According to the squeeze container 1 of the present embodiment, the sheet-shaped elastic body 3 can be gradually swelled to the storage portion 2 side by repeating squeezing of the squeeze deformation portion 15 and releasing of the squeezing in a state that a content 33 such as liquid or gel is filled into the storage portion 2. Accordingly, an amount or speed of delivering the content can be arbitrarily controlled by appropriately controlling an amount or speed of swelling the elastic body 3.

Further, being different from the containers of Patent Literature 1 and Patent Literature 2, since the content 33 is squeezed and delivered by the elastic body 3, it is possible to stably deliver an appropriate amount of content even when the content 33 becomes less. Here, in the squeeze container 1 of the present embodiment, the sheet-shaped elastic body 3 which has been plane-shaped at the beginning can be swelled until becoming to a solid shape (solid shape being like a slightly irregular hemisphere) along the shape of the inner face of the storage portion 2.

Here, storing and filling of the content 33 into the storage portion 2 may be performed with the cover body 7 detached or via the delivery passage 5 without detaching the cover body 7.

Further, in the squeeze container 1 of the present embodiment, the partition wall 23 which is hardly deformed even when the squeeze deformation portion 15 is deformed is provided between the squeeze deformation portion 15 and the elastic body 3. Accordingly, an amount of air fed toward the elastic body 3 due to one time of pressing of the squeeze deformation portion 15 can be prevented from being largely fluctuated for each pressing.

The squeeze container 1 of the present embodiment includes the air-bleeding device 24 which discharges air accumulated in a space 34 between the partition wall 23 and the elastic body 3 to the outside after delivering the content 33. The air-bleeding device 24 includes a communication passage 35 which provides communication between the space 34 and the outside of the container and a plug member 36 which is arranged at an opening portion at the outer side of the communication passage 35 and opens and closes the opening portion. The plug member 36 is continuously urged upward by a coil spring 37 and closes the opening portion at the outer side of the communication passage 35 in a normal state (state that the plug member 36 is not pressed from the upper side). When the plug member 36 is pressed from the upper side, the opening portion is opened and air in the communication passage 35 is discharged to the outside through the communication passage 35. Therefore, after content applying operation is completed, the swelled elastic body 3 can be easily returned into an original state illustrated in FIG. 2 with simple operation. Accordingly, the applying operation can be easily restarted. In addition, elastic restoration force of the elastic body 3 can be easily prevented from being lost owing to that the elastic body 3 is left in a swelled state.

The squeeze container 1 of the present embodiment includes the container body 6 and the cover body 7 which is fixed to the container body 6 in a detachably attachable manner. The storage portion can be opened by detaching the cover body 7. The concave storage portion 2 includes the approximately-circular opening portion 2a and a curved concave inner face 41. The depth d1 of the storage portion is smaller than the diameter d2 of the storage portion 2 at the center part of the storage portion in the depth direction. Accordingly, in a case that the squeeze container is used for applying hair dye to hair as storing the hair dye in the storage portion 2, cleaning operation necessary when changing hair dye colors is facilitated compared to a traditional bottle-shaped container.

Further, the squeeze container 1 of the first embodiment (as well as later-mentioned containers 1', 1A, 10, 1B) can deliver the content as squeezing the squeeze deformation portion 15 with one hand as holding the container with the one hand. Here, "the one hand" denotes the right hand when being held by the right hand and denotes the left hand when being held by the left hand.

Accordingly, in a case of filling a treating agent for hair or scalp such as hair dye like hair color etc., a hair growing agent, a hair dressing agent, a shampoo and a massage agent as the content, for example, and applying the treating agent to hair, it is easy to perform applying operation while changing sections to be applied. Further, it is also possible to concurrently perform other operation with the hand by which the container is not held while performing the applying operation using the squeeze container.

Examples of the content to be stored in the squeeze container and to be delivered include stationery such as paints, food such as mayonnaise and ketchup, and the like as well as the abovementioned treating agent for hair or scalp. Here, the content in the present invention (first to eighth inventions) is not limited to the above.

Further, in the squeeze container 1 of the present embodiment (as well as the squeeze containers 1', 1A of a second embodiment), the elastic body 3 can be swelled until the approximate whole is abutted to the inner face of the storage portion 2 by repeating squeezing of the squeeze deformation portion 15 and releasing thereof. Accordingly, almost the all amount of the content 33 can be delivered.

In the light of delivering the content stored in the storage portion 2 without leftover, it is preferable that the solid shape of an inner face 41 of the storage portion 2 is designed to be matched with the solid shape of the elastic body 3 when the elastic body 3 is swelled to be a predetermined size.

Examples of a specific method to actualize the above include a method to process the inner face 41 of the storage portion 2 so that the elastic body 3 is abutted approximately concurrently to the whole range of the inner face 41 while observing the abutting state of the swelled elastic body as molding the container body 6 with transparent material.

For example, with a method described below, it is possible to determine whether or not the solid shape of the inner face 41 of the storage portion 2 is matched with the solid shape of the elastic body 3 when the elastic body 3 is swelled to the predetermined size.

That is, the content is filled into the storage portion and is delivered by swelling the elastic body, and then, existence of the content is checked at the time when the delivering is stopped. In a case that the content remains, a remaining state of the content is observed.

Figure 5:
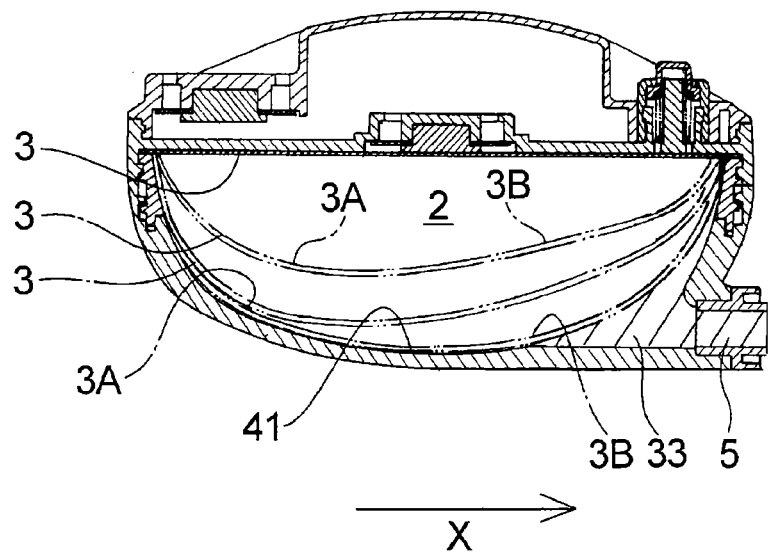
FIG. 5 is an explanatory view of a preferable embodiment of the present invention.

Further, in the light of delivering without leftover of the content stored in the storage portion 2, it is preferable that the elastic body 3 is structured so that a section 3A thereof being far from the delivery passage 5 is to be swelled earlier than a section 3B thereof being close to the delivery passage 5 in a content delivery direction (X-direction) as illustrated in FIG. 5 by unequalizing thickness thereof. According to the above, it is possible to effectively push out the content in the delivery direction (X-direction) and the amount of content remaining in the storage portion can be remarkably decreased.

Figure 6A:
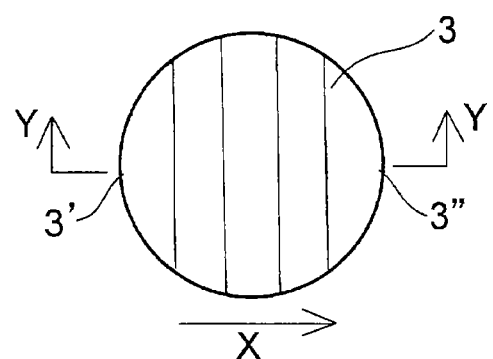
FIGS. 6(a) and 6(b) are views respectively illustrating an elastic body to be used for a preferable embodiment of the present invention and FIG. 6(c) is a sectional view at line Y-Y of FIG. 6(a).
Figure 6B:
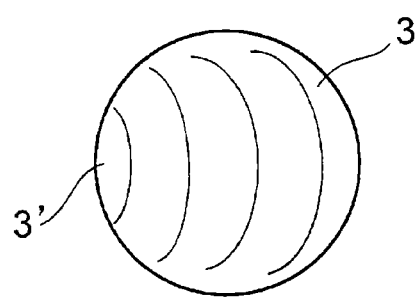
Figure 6C:
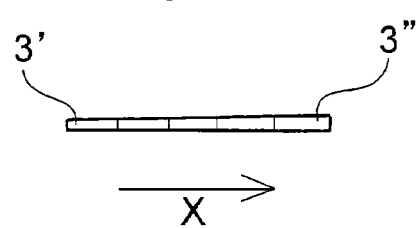

The elastic body 3 illustrated in FIG. 6(a) has thickness which is gradually increased from one end 3' being the farthest from the delivery passage 5 toward the other end 3" in the X-direction. The elastic body 3 illustrated in FIG. 6(b) has thickness which is gradually increased in a radiation direction from one end 3' being the farthest from the delivery passage 5. Owing to using such an elastic body, the elastic body 3 can be structured so that the section 3A being far from the delivery passage 5 is swelled earlier than the section 3B being close to the delivery passage 5, as illustrated in FIG. 5.

Here, the content delivery direction (X-direction) denotes a direction from the farthest section of the elastic body 3 from the delivery port 27 toward the closest section thereof to the delivery port 27.

Next, second and third inventions will be described based on a squeeze container 1' of the second embodiment illustrated in FIGS. 7 to 17 which is also an embodiment of any of the first to third inventions.

Figure 8:
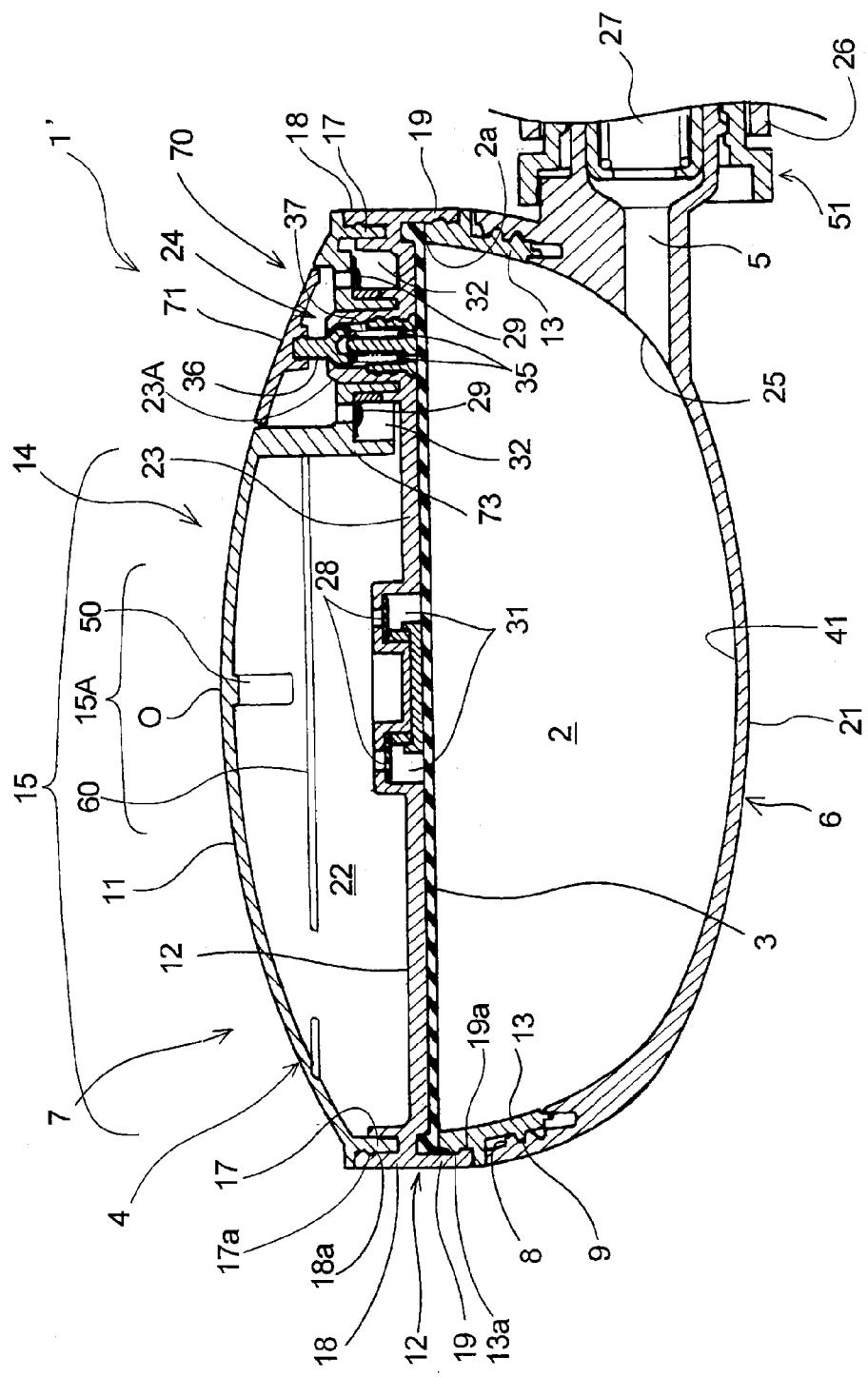
FIG. 8 is an enlarged sectional view at line I-I of FIG. 7.

As illustrated in FIG. 8, the squeeze container 1' of the second embodiment of the present invention includes a concave storage portion 2 in which a content is stored, a sheet-shaped elastic body 3 which is arranged on the storage portion 2, pressurization means 4 which swells the elastic body 3 toward the storage portion 2 side with air pressure (gas pressure), and a delivery passage 5 which provides communication between the inside and outside of the storage portion 2 and which delivers the content squeezed by the elastic body 3 to the outside.

The storage portion 2 is concaved, more specifically, concaved to be a hemispherical or partially-spherical shape and has an approximately-circular opening portion 2a at an upper face thereof. The sheet-shaped elastic body 3 is arranged to cover the whole opening portion 2a of the storage portion 2. Further, the concave storage portion of the present invention may have larger sectional area at the inside thereof than area at the opening portion. Further, as in the squeeze container 1' of the present embodiment, it is preferable that the concave storage portion has an approximately-circular opening portion and a curved concave bottom face and that a depth of the storage portion is smaller than a diameter of the storage portion at a center part of the storage portion in the depth direction.

Figure 9:
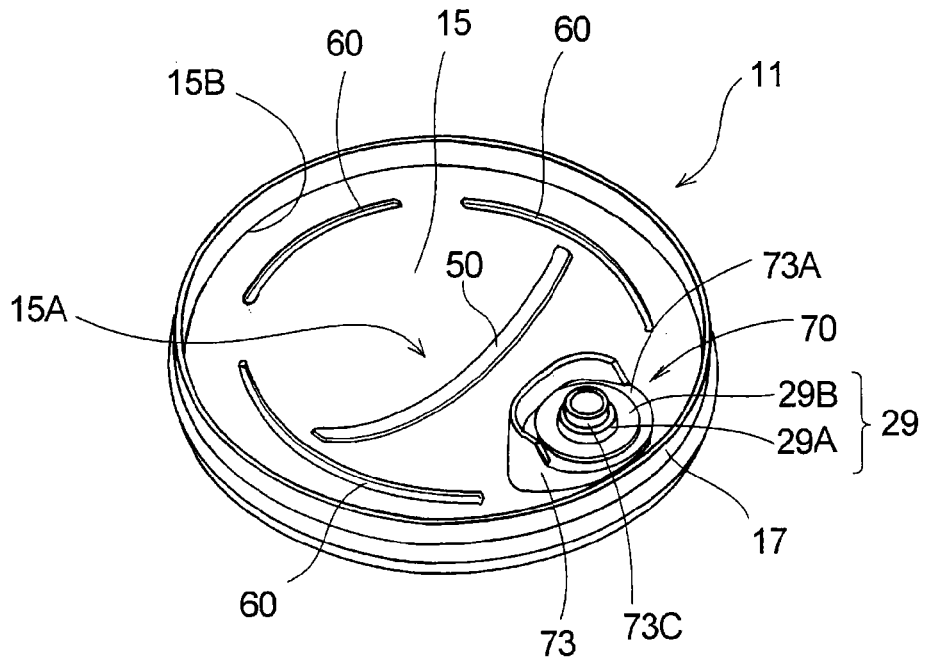
FIG. 9 is a perspective view illustrating an inside of a squeeze deformation portion.

The pressurization means 4 includes a squeeze deformation portion 15 which is deformed by squeezing with a hand and which is returned into an original state by releasing of the squeezing and is structured to swell the elastic body 3 by squeezing and deforming the squeeze deformation portion 15. The squeeze deformation portion 15 is formed like a curved convex face toward the outside of the container and includes a linear reinforcement portion 50 which traverses an apex portion 15A of the squeeze deformation portion 15 and a linear thin-walled portion 60 which is formed in a direction along a circumferential edge 15B of the squeeze deformation portion 15, as illustrated in FIG. 9. The reinforcement portion 50 of the present embodiment is a convex rib and is formed at the inner face side of the squeeze deformation portion 15. Further, the thin-walled portion 60 is formed by arranging a concave groove at the inner face side of the squeeze deformation portion 15. The pressurization means 4 is structured so that the elastic body 3 can be gradually swelled by repeating squeezing and releasing of the squeeze deformation portion 15.

Further, pressurization means 4 includes the squeeze deformation portion 15 which is deformed by squeezing with a hand and which is returned into an original state by releasing of the squeezing and a second check valve 29 which opens an intake passage 32 to suck outer air when the squeezing is released. The pressurization means 4 is structured so that the elastic body 3 can be gradually swelled by feeding air into an inflation chamber 34 of which part is structured by the elastic body 3 by repeating squeezing and releasing of the squeeze deformation portion 15.

Further, the squeeze container 1' includes an air-bleeding device 24 which discharges air in the inflation chamber 34 to the outside. The air-bleeding device 24 includes a coil spring (elastic member) 37, a plug member 36, and a communication passage 35 which provides communication between the inside of the inflation chamber 34 and the outside of the container 1' via a storage portion 77A of the coil spring 37. The plug member 36 closes the communication passage 35 as being urged by the coil spring 37 and opens the communication passage 35 when being pressurized. The intake passage 32 which is opened and closed by the second check valve 29 surrounds a periphery of the air-bleeding device 24.

In the following, the squeeze container 1' of the second embodiment will be described more specifically.

Figure 7:
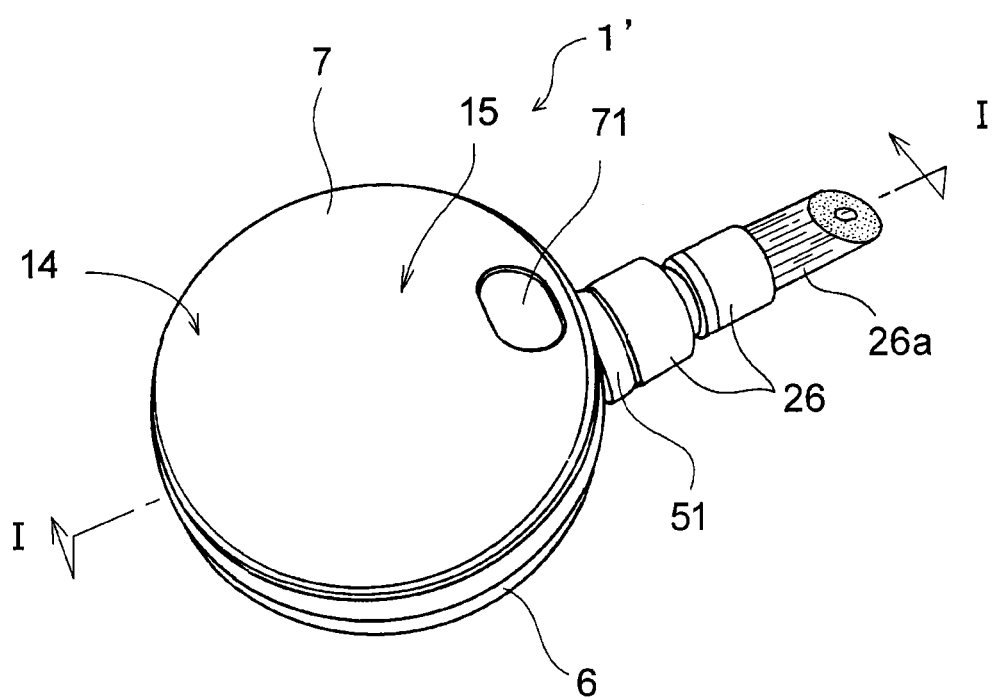
FIG. 7 is a perspective view illustrating a second embodiment of a squeeze container of the present inventions (first to third embodiments).

As illustrated in FIG. 7, the squeeze container 1' roughly has a shape like a flat spherical body, more specifically, like a flat ellipsoidal body, so that content squeeze operation can be performed by one hand while holding with the one hand. Here, the flat ellipsoidal body denotes a solid of revolution obtained as having a short axis of an ellipse as a rotating axis.

The squeeze container 1' includes a container body 6 which has a curved concave inner face and a cover body 7 which is attached to the container body 6 in a detachably attachable manner. As illustrated in FIG. 8, the container body 6 includes a screwing convex stripe portion 8 at an inner circumferential face at an upper end part thereof and the cover body 7 includes a screwing convex stripe 9 at an outer circumferential face at a lower end part. The container body 6 and the cover body 7 are screwed via the screwing convex stripe portion 8 and the screwing convex stripe 9 as being detachably attachable.

The cover body 7 includes a top face portion forming member 11, a partition wall forming member 12, the sheet-shaped elastic body 3, and an elastic body fixing member 13.

The top face portion forming member 11 forms a curved convex top face portion 14 which is convexed toward the outside of the squeeze container 1'. The whole top face portion 14 forms a squeeze deformation portion 15 which is easily deformed by squeezing with a hand and is returned into an original state by releasing of the squeezing. That is, the squeeze deformation portion 15 has a curved convex shape.

A cylindrical connection portion 17 is vertically arranged at a peripheral part of the top face portion forming member 11 in a direction opposite to a swelling direction of a curved convex face of the squeeze deformation portion 15. A pair of cylindrical connection portions 18, 19 extended vertically is arranged at a peripheral part of the partition wall forming member 12. The top face portion forming member 11 and the partition wall forming member 12 are integrated as being air-tightly connected by screwing the cylindrical connection portion 17 of the top face portion forming member 11 and the cylindrical connection portion 18 extended upwardly at the peripheral part of the partition wall forming member 12 via a screwing convex stripe 17a and a screwing concave stripe 18a which are arranged respectively. Owing to the connection described above, a pressurization chamber 22 is formed between the top face portion forming member 11 and the partition wall forming member 12.

Figure 10:
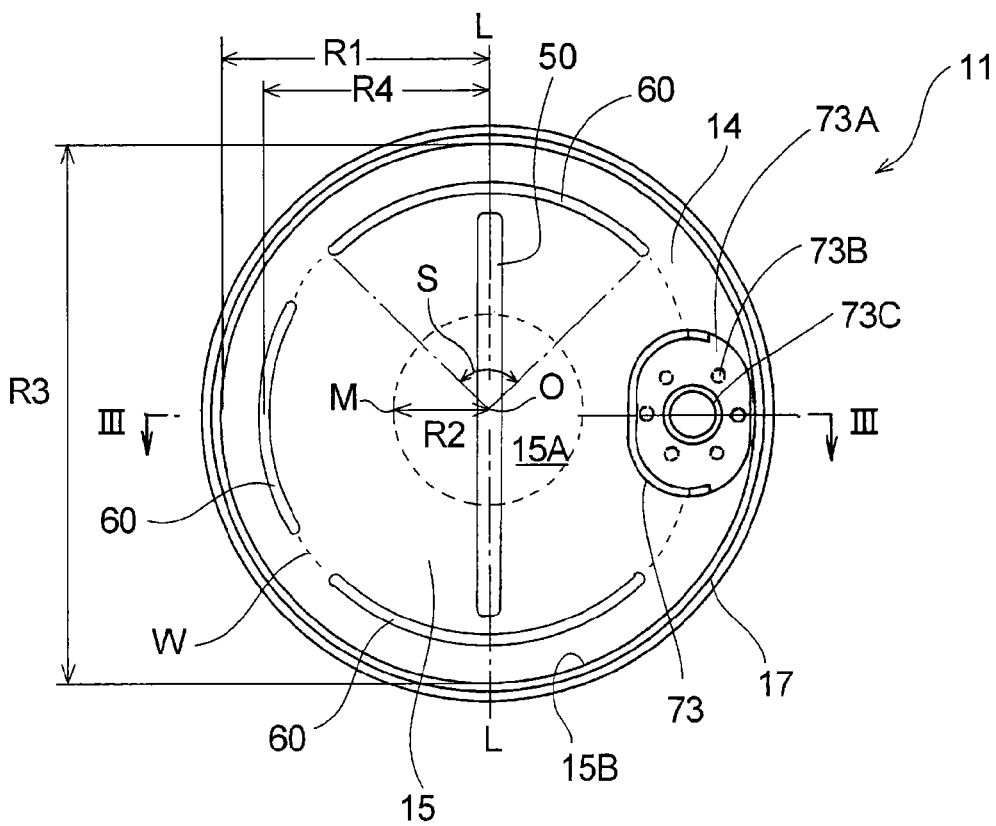
FIG. 10 is a plane view of a top face portion forming member viewing from the inside thereof.
Figure 11:
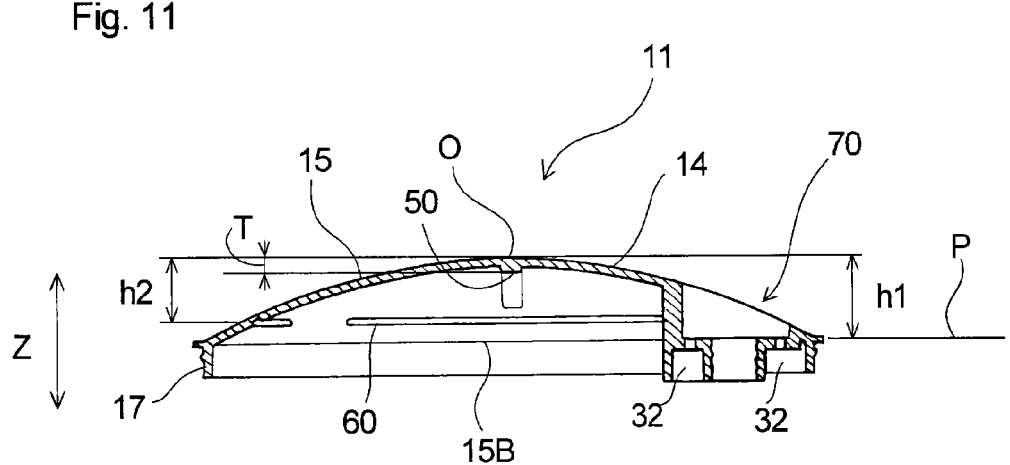
FIG. 11 is a sectional view at line of FIG. 10.

The squeeze deformation portion 15 of the squeeze container 1' of the present embodiment will be specifically described. As illustrated in FIG. 10, the squeeze deformation portion 15 has a circular shape in plane view as having the apex O of the curved convex face as the center thereof. The circumferential edge 15B of the squeeze deformation portion 15 is a circumference as having the apex O as the center thereof. As illustrated in FIG. 11, the squeeze deformation portion 15 is shaped into a curved convex face as being arc-shaped in sectional view. In the squeeze deformation portion 15, the apex O is the point having the maximum length against a plane P passing through the circumferential edge 15B in a direction perpendicular to the plane P (z-direction in FIG. 11). In FIG. 11, the distance from the apex O to the plane P in z-direction is denoted by height h1. Here, thickness of the squeeze deformation portion 15 except positions where the later-mentioned reinforcement portion 50 and the thin-walled portion 60 are formed is approximately equaled.

As illustrated in FIGS. 9 and 10, the squeeze deformation portion 15 includes the linear reinforcement portion 50 which traverses the apex portion 15A and the linear thin-walled portion 60 which is formed in the direction along the circumferential edge 15B.

Owing to that the reinforcement portion 50 and the thin-walled portion 60 are formed at the squeeze deformation portion 15, the squeeze deformation portion 15 is improved in deformability due to squeezing and in restoration characteristics from a deformed state. Accordingly, content delivering operation can be performed more smoothly.

For example, the apex portion 15A of the squeeze deformation portion 15 where the reinforcement portion 50 traverses denotes a range surrounded by a dotted line M drawn on positions with the distance R2 from the apex O being one third of the distance R1 from the apex O of the squeeze deformation portion 15 to the circumferential edge 15B in plane view. As illustrated in FIG. 10, the apex portion 15A has a shape in plane view being homothetic to a shape of the circumferential edge 15B of the squeeze deformation portion 15 in plane view. In a case of the squeeze deformation portion 15 being circular in plane view as illustrated in FIG. 10, the apex portion 15A also has a circular shape in plane view.

As illustrated in FIGS. 9 and 10, the reinforcement portion 50 of the present embodiment being an elongated convex rib is singly formed at the squeeze deformation portion 15. The reinforcement portion 50 is formed like an arc shape along the curved convex portion of the squeeze deformation portion 15 as being linear in plane view. Further, the reinforcement portion 50 being the convex rib is protruded to the inner face side of the squeeze deformation portion 15.

Further, the reinforcement portion 50 is formed to be along a line in the radial direction of the squeeze deformation portion 15 in plane view as traversing the apex O of the squeeze deformation portion 15. The distance between the center line L of the reinforcement portion 50 and the apex O is preferably 5 mm or less, and more preferably, 2 mm or less. In the example illustrated in FIG. 10, the center line L of the reinforcement portion and the apex O are overlapped, so that the distance therebetween is zero. Thus, even more preferably, the center line L of the reinforcement portion 50 is overlapped with the apex O. The center line L of the reinforcement portion 50 is a straight line which bisects the reinforcement portion 50 in width as being extended in the longitudinal direction of the reinforcement portion 50.

As illustrated in FIG. 10, it is preferable that the reinforcement portion 50 is formed in a direction so that the center line L is not to be overlapped with an integrated valve device 70 from a viewpoint that the reinforcement portion 50 can be elongated in the longitudinal direction as described later. As illustrated in FIG. 10, the reinforcement portion 50 of the present embodiment is formed to be approximately in parallel to an outer face of a cylindrical wall 73 of the later-mentioned integrated valve device 70 at the apex O side.

It is preferable that the length of the reinforcement portion 50 in the longitudinal direction is determined from viewpoints to facilitate returning of the squeeze deformation portion 15 from a deformed state into an original state and not to arrive at the thin-walled portion 60 which is formed at the vicinity of the circumferential edge of the squeeze deformation portion 15 to improve deformability. Specifically, the length of the reinforcement portion 50 in the longitudinal direction is preferably in a rage between 50% and 80%, more preferably 60% and 70% of the length R3 of the squeeze deformation portion 15. The length R3 of the squeeze deformation portion 15 denotes a length from one end to the other end of the squeeze deformation portion 15 (distance of the squeeze deformation portion in plane view) on the straight line passing through the apex O. In a case that the squeeze deformation portion 15 is not circular but long in one direction, the distance R3 denotes a distance in plane view from one end to the other end on a straight line passing through the apex O in the same direction as the longitudinal direction of the reinforcement portion 50. The length of the reinforcement portion 50 in the longitudinal direction denotes a distance of the squeeze deformation portion 15 in plane view as well.

It is preferable that the reinforcement portion 50 does not arrive at a circular line W (see FIG. 10) where the thin-walled portion 60 is arranged from a viewpoint not to disturb bending due to the thin-walled portion 60.

Further, thickness T (see FIG. 11) of the squeeze deformation portion 15 at a part having the reinforcement portion 50 is preferably in a range between 120% and 200%, more preferably between 140% and 160% against thickness at a part other than the part having the reinforcement portion and the thin-walled portion of the squeeze deformation portion. Further, width of the reinforcement portion is preferably in a range between 1 mm and 10 mm, and more preferably, in a range between 2 mm and 4 mm.

Here, in the present embodiment, the reinforcement portion 50 (convex rib) is formed to have approximately constant thickness in both directions of the width direction and the longitudinal direction, as illustrated in FIG. 11. However, the thickness of the reinforcement portion 50 may be varied in the width direction. For example, the sectional shape of the reinforcement portion may be a trapezoid, a sectional circle, a triangle or the like. Further, the thickness of the reinforcement portion 50 may be varied in the longitudinal direction and may be structured to be thin as being apart from the apex O, for example.

Further, in the present embodiment, the reinforcement portion 50 is the convex rib which is integrated with the squeeze deformation portion 15. However, it is also possible to form the reinforcement portion by fitting or bonding a separate member. For example, the reinforcement portion 50 may be formed by fixing a member formed separately from the squeeze deformation portion 15 to the inner face or the outer face of the squeeze deformation portion 15 with bonding, welding or the like. Material of the reinforcement portion 50 may be the same as later-mentioned material of the squeeze deformation portion 15 (top face portion 14) or may be different therefrom. Here, it is preferable that the reinforcement portion 50 is integrally molded with the squeeze deformation portion 15 from a viewpoint of improving productivity.

As illustrated in FIGS. 9 and 10, the thin-walled portion 60 of the present embodiment is formed linearly extended in a direction along the circumferential edge 15B of the squeeze deformation portion 15. The thin-walled portion 60 is preferably formed at a position being apart from the circumferential edge 15B by a predetermined width. For example, in plane view, the distance R4 between the thin-walled portion 60 and the apex O is preferably in a range between 60% and 90%, more preferably in a range between 70% and 80% of the distance R1 between the apex O and the circumferential edge 15B.

Further, the thin-walled portion 60 is formed at height h2 from the thin-walled portion 60 to the apex O preferably being in a range between 60% and 90% against the height h1 from the plane P to the apex O, and more preferably, in a range between 70% and 80%. Owing to being 90% or less, forming the thin-walled portion 60 can reliably provide an effect to facilitate returning of the squeeze deformation portion 15 from a deformed state into an original state. Owing to being 60% or more, it is advantageous in ensuring a length of the reinforcement portion 50 as well as enlarging a swell amount of the elastic body with one squeezing. Here, the height denotes a distance in z-direction. In the present embodiment, the thin-walled portion 60 is approximately in parallel to the circumferential edge 15B in side sectional view and the height h2 from the thin-walled portion 60 to the apex O is approximately constant.

The thin-walled portion 60 of the present embodiment is formed by arranging a concave groove having a predetermined width and a predetermined depth at the inner face side of the squeeze deformation portion 15. The thin-walled portion 60 and the concave groove which forms the thin-walled portion 60 are linearly formed as being extended in a direction along the circumferential edge 15B. The sectional shape of the concave groove may be an arbitrary shape such as a triangle, a trapezoid, semicircle and semi-oval. In the present embodiment, the width and thickness of the thin-walled portion are approximately constant along the circular line W. However, not being necessarily to be like the above, the thin-walled portion 60 may be formed thinner at a position for particularly desirable folding. The thickness of the thin-walled portion 60 is preferably in a range between 30% and 70% against thickness at sections other than the reinforcement portion 50 of the squeeze deformation portion 15, and more preferably, in a range between 40% and 60%. Owing to being 70% or less, forming the thin-walled portion 60 can reliably provide an effect to improve folding characteristics. Owing to being 30% or more, sufficient strength can be ensured at the folding part. Further, it is preferable that the width of the thin-walled portion 60 (width at a surface of the squeeze deformation portion 15) is in a range between 0.5 mm and 2 mm.

In the present embodiment, the thin-walled portion 60 is formed like discontinued lines. That is, the thin-walled portion 60 is arc-shaped as being divided into three sections. If the arc-shaped sections of the thin-walled portion 60 are extended, a circular line W being a circle formed of a single line along the circumferential edge 15B is formed. Accordingly, a continued folding line is formed on the circular line W when the squeeze deformation portion 15 is squeezed, so that folding can be easily performed at the thin-walled portion 60. In the present embodiment, the circular line W forms a circle in plane view. The sum of angles S (see FIG. 10) formed with both ends of each arc-shaped thin-walled portion 60 and the apex O is preferably in a range between 180° and 270°, that is, in a range between 50% and 75% against 360°.

The thin-walled portion 60 may be linearly formed like a single continuous line. In the present embodiment, the integrated valve device 70 exists on the circular line W, as illustrated in FIG. 10. If the integrated valve device 70 does not exist on the circular line W, for example, the thin-walled portion 60 may be formed like a single continuous circular line.

In the present embodiment, the outer face of the squeeze deformation portion 15 can be formed into an even face by forming the convex rib which forms the reinforcement portion 50 and the concave groove which forms the thin-walled portion 60 at the inner face side of the squeeze deformation portion 15. The above is preferable in a viewpoint of improving appearance of the container 1' and the like. Here, either or both of the reinforcement portion 50 and the thin-walled portion 60 may be formed at the outer face of the squeeze deformation portion 15 to form the convex portion or the concave portion.

A structure of the squeeze container 1' other than the squeeze deformation portion will be described.

Figure 12:
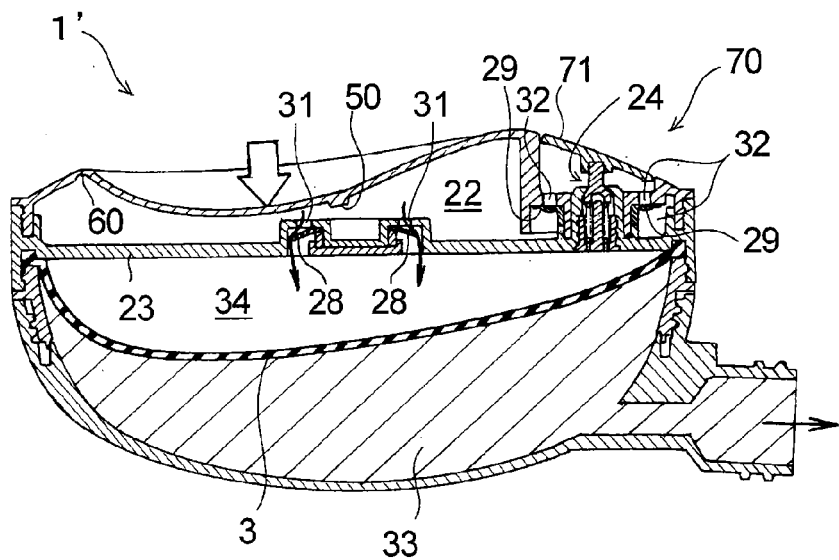
FIG. 12 is a sectional view illustrating a squeeze-deformed state of the squeeze deformation portion of the squeeze container of FIG. 7.

The partition wall forming member 12 forms a flat-plate-shaped partition wall 23, which is circular in plane view, between the pressurization chamber 22 and the sheet-shaped elastic body 3. As illustrated in FIG. 12, there is substantially no deformation at the partition wall 23 even when the squeeze deformation portion 5 is deformed by being squeezed with a hand.

The sheet-shaped elastic body 3 is arranged along the partition wall 23 as being closed to the partition wall 23. In other words, one face of the partition wall 23 is covered with the elastic body 3. The sheet-shaped elastic body 3 is fixed at a peripheral part thereof being sandwiched at a space between the partition wall forming member 12 and the elastic body fixing member 13. The sheet-shaped elastic body 3 is not fixed to the partition wall forming member 12 other than the peripheral part. Accordingly, as illustrated in FIG. 12, the sheet-shaped elastic body 3 is swelled to the storage portion 2 side with pressure (air pressure) of air fed by the pressurization means 4.

The partition wall forming member 12 and the elastic body fixing member 13 are integrated by screwing the elastic body fixing member 13 and the cylindrical connection portion 19 extended downwardly at the peripheral part of the partition wall forming member 12 via the screwing convex stripes 19a, 13a which are arranged respectively thereto.

The elastic body fixing member 13 is cylindrical and an inner circumferential face thereof forms a curved concave face which is continued to the curved concave inner face of the container body 6. The curved concave inner face 41 of the concave storage portion 2 is formed with the inner face of the elastic body fixing member 13 and the curved concave inner face of the container body 6. An opening portion 25 of the delivery passage 5 at the storage portion 2 side is opened into a circular or oval shape at a part of the curved concave inner face 41 of the storage portion 2, more specifically, at a part positioning right below the integrated valve device 70 which is described later.

Figure 13:
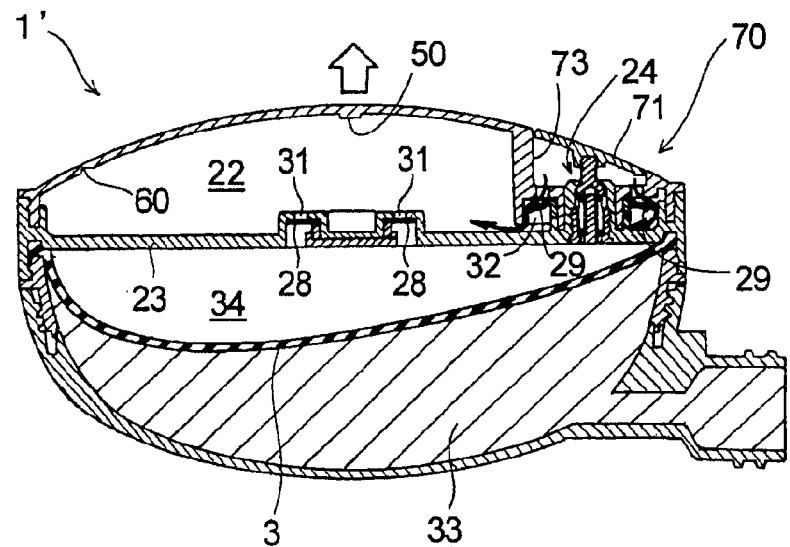
FIG. 13 is a sectional view illustrating a state that the squeeze deformation portion of the squeeze container of FIG. 7 is returned from a deformed state into an original state.
Figure 14:
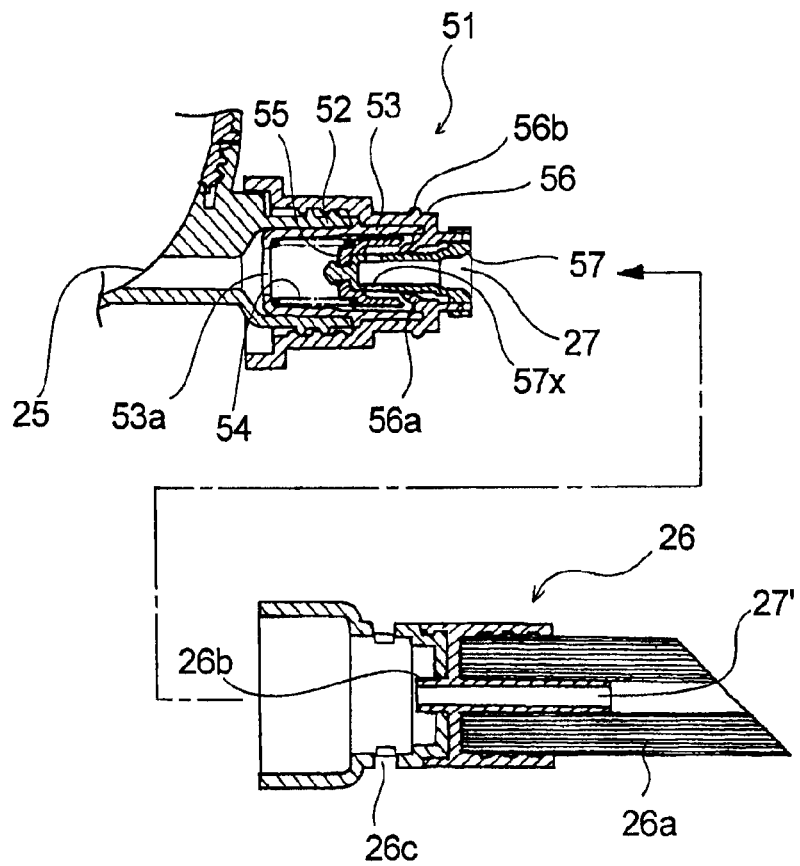
FIG. 14 is a sectional view illustrating a structure in the vicinity of a delivery passage of the container of FIG. 7 in a state that a nozzle member is separated from a filling-delivering portion.

As illustrated in FIGS. 13 and 14, a nozzle member 26 is fixed to the delivery passage 5 in a detachably attachable manner via a filling-delivering portion 51 which is protruded from an outer circumferential section of the container body 6. The filling-delivering portion 51 has a flow passage of fluid at the inside thereof. The filling-delivering portion 51 opens the flow passage in a state that the nozzle member 26 is attached and closes the flow passage in a state that the nozzle member 26 is not attached. As illustrated in FIG. 14, an opening portion 27 at the outer side of the delivery passage 5 is formed at the filling-delivering portion 51. An opening portion 27' for content delivery is formed at the nozzle member 26. The nozzle member 26 is to be used for delivering a content 33 in the container 1'. Owing to replacement thereof, it is possible to be replaced with a nozzle member being different in length or diameter of a passage communicated to the opening portion 27', dimensions of the opening portion 27', or the like. It is also possible to replace a brush-equipped nozzle member having a brush 26a at a periphery thereof with a nozzle member without such a brush.

Figure 17:
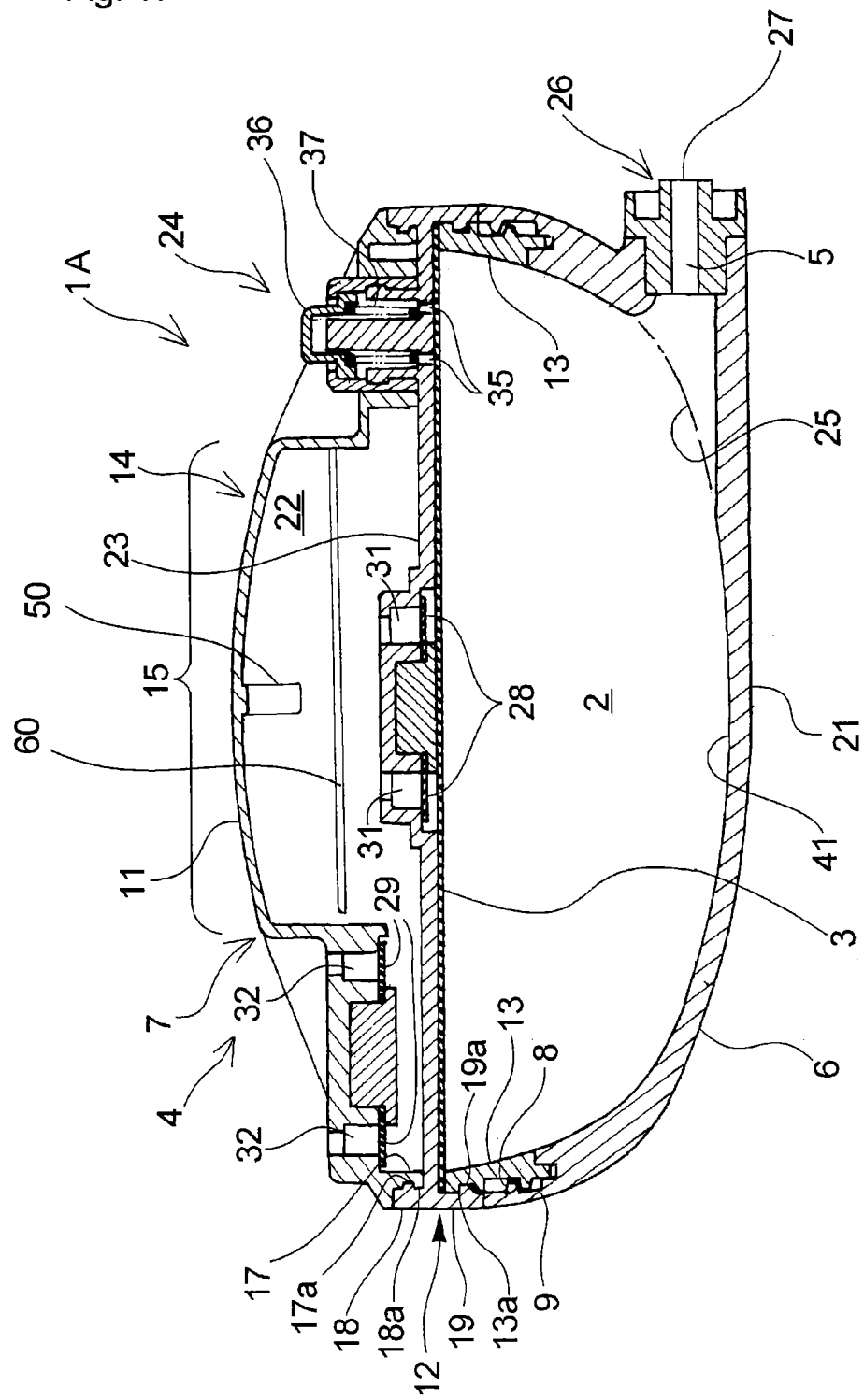
FIG. 17 is a sectional view (corresponding to FIG. 8) further illustrating another embodiment of the present invention.

Here, as an embodiment illustrated in FIG. 17, the delivery passage 5 may be formed by fixing the nozzle member 26 directly to a member which forms a bottom face portion 21 of the container body 6 in a permanently-set manner or a detachably attachable manner.

As illustrated in FIG. 14, the filling-delivering portion 51 includes a cylindrical connection portion 52, a closed-end cylindrical coil spring holding body 53 having a penetration hole 53a at the center of a bottom portion thereof as the bottom portion side being inserted into the cylindrical connection portion 52, a coil spring 54, a closed-end cylindrical valve member 55 which is accommodated in the coil spring holding body 53 in a state of being urged in a direction toward the opening portion 27 by the coil spring 54, a valve enclosure body 56 which fixes the coil spring holding body 54 at a predetermined inner position as being screwed to an outer circumferential section of the cylindrical connection portion 52 and which closes a flow passage between the opening portion 25 and the opening portion 27 as having a valve abutment portion 56a extended into the coil spring holding body 53 intimately contacted to an opening peripheral part of the valve member 55, and a nozzle connection member 57 of which bottom portion is coupled with a bottom portion of the valve member 55 as having a plurality of penetration holes 57x structuring a part of the flow passage at a circumferential wall in the vicinity of the bottom portion.

In the filling-delivering portion 51, the valve member 55 is intimately contacted to the valve abutment portion 56a of the valve enclosure body 56 and the flow passage between the opening portion 25 and the opening portion 27 is closed in a state that the nozzle member 26 is not attached thereto and in a state that a fluid filling nozzle of an aerosol container or a pump-type container is not pressed thereto.

On the contrary, for attaching the nozzle member 26, the cylindrical connection portion 26b of the nozzle member 26 presses the nozzle connection member 57, and then, the nozzle connection member 57 and the valve member 55 coupled thereto are pressed toward the container body 6 side against urging force of the coil spring 54. Accordingly, the opening portion 25 and the opening portion 27 are in a communicated state and the delivery passage 5 for the passage 33 is in an opened state from the opening portion 25 to the opening portion 27' for content delivery in the nozzle member. Here, a convex portion 56b arranged at an outer circumferential section of the valve enclosure body 56 and a groove or an opening portion 26c for locking arranged at the nozzle member 26 are engaged by twisting the nozzle member 26 after covering the valve enclosure body 56. Accordingly, the coupling state with the valve enclosure body 56 and the flow passage from the opening portion 25 to the opening portion 27' are stably maintained.

Storing and filling of the content 33 into the storage portion 2 may be performed with the cover body 7 removed or via the delivery passage 5 without detaching the cover body 7.

In a case of filling via the delivery passage 5, the nozzle connection member 57 is pressed by a discharge port of a pump-type injector or an aerosol container, for example. In this case as well, the nozzle connection member 57 and the valve member 55 coupled thereto are pressed toward the container body 6 side. Accordingly, the opening portion 25 and the opening portion 27 which is to be a filling port are to be in a communicated state.

The pressurization means 4 is means to swell the sheet-shaped elastic member 3 to the storage portion 2 side with air pressure. The pressurization means 4 of the squeeze container 1' of the present embodiment includes a first check valve 28 and a second check valve 29 in addition to the squeeze deformation portion 15, the air chamber 22 and the partition wall 23 which are described above.

The first check valve 28 is arranged at a communication passage 31 which is formed at the partition wall 23 and feeds air in the pressurization chamber 22 toward the elastic body 3 as opening the communication passage 31 when the squeeze deformation portion 15 is deformed as being squeezed with a hand as illustrated in FIG. 12. On the other hand, when the squeezing of the squeeze deformation portion 15 is released as illustrated in FIG. 13, the communication passage 31 is closed by the first check valve 28 and the air swelling the elastic body 3 is prevented from being regurgitated to the pressurization chamber 22 accordingly.

The second check valve 29 is arranged at an intake passage 32 which is formed at the top face portion forming member 11 and closes the intake passage 32 when the squeeze deformation portion 15 is deformed as being squeezed with a hand as illustrated in FIG. 12. When the squeezing is released after squeezing the squeeze deformation portion 15 as illustrated in FIG. 13, the squeeze deformation portion 15 is returned into an original state owing to restoration characteristics thereof. Then, the second check valve 29 opens the intake passage 32 and air outside the squeeze container 1' inflows into the pressurization chamber 22.

As illustrated in FIG. 12, when the squeeze deformation portion 15 is to be deformed by being squeezed with a hand, the squeeze deformation portion 15 is folded easily and reliably at the thin-walled portion 60. Accordingly, the squeeze deformation portion 15 can be deformed largely with a small force. Further, as illustrated in FIG. 13, when squeezing of the squeeze deformation portion 15 is released, a section where the reinforcement portion 50 is arranged becomes a starting point of movement to return into an original state. Accordingly, the squeeze deformation portion 15 can be quickly returned into an original state.

Next, the integrated valve device 70 arranged at the cover body 7 will be described based on FIGS. 8, 15 and the like. In the integrated valve device 70 of the present embodiment, the air-bleeding device 24 and the second check valve 29 are integrated so that the intake passage 32 which is opened and closed by the second check valve 29 surrounds the communication passage 35 of the air-bleeding device 24. Here, the air-bleeding device 24 is a device to discharge air accumulated in the inflation chamber 34 to the outside after delivering the content 33. Further, the communication passage 35 provides communication between the outside of the container and the inside of the inflation chamber 34.

The inflation chamber 34 of the present embodiment is a space between the partition wall 23 and the elastic body 3. In an initial state before squeezing the squeeze deformation portion 15, there does not exist a space being anything like a chamber between the partition wall 23 and the sheet-shaped elastic body 3 as the both being intimately contacted. However, the inflation chamber in the present application includes this space between the partition wall 23 and the sheet-shaped elastic body 3 which are in an intimately contacted state. Here, it is also possible that a gap or a space having predetermined volume exists between the partition wall 23 and the elastic body 3 from the initial state before squeezing the squeeze deformation portion 15.

The integrated valve device 70 being an embodiment of an intake-discharge integrated valve device of the present invention (fourth invention) includes a plurality of intake penetration holes (intake holes) 73B with the second check valve 29 and the communication passage for discharge (discharge passage) 25 which is surrounded by the penetration holes (intake holes) 73B and which is opened and closed with displacement of the plug member 36 urged by the coil spring 37 (elastic member). A spring holding portion (a storage portion of the elastic member) which stores the coil spring 37 structures a part of the communication passage for discharge (discharge passage) 35.

Figure 15:
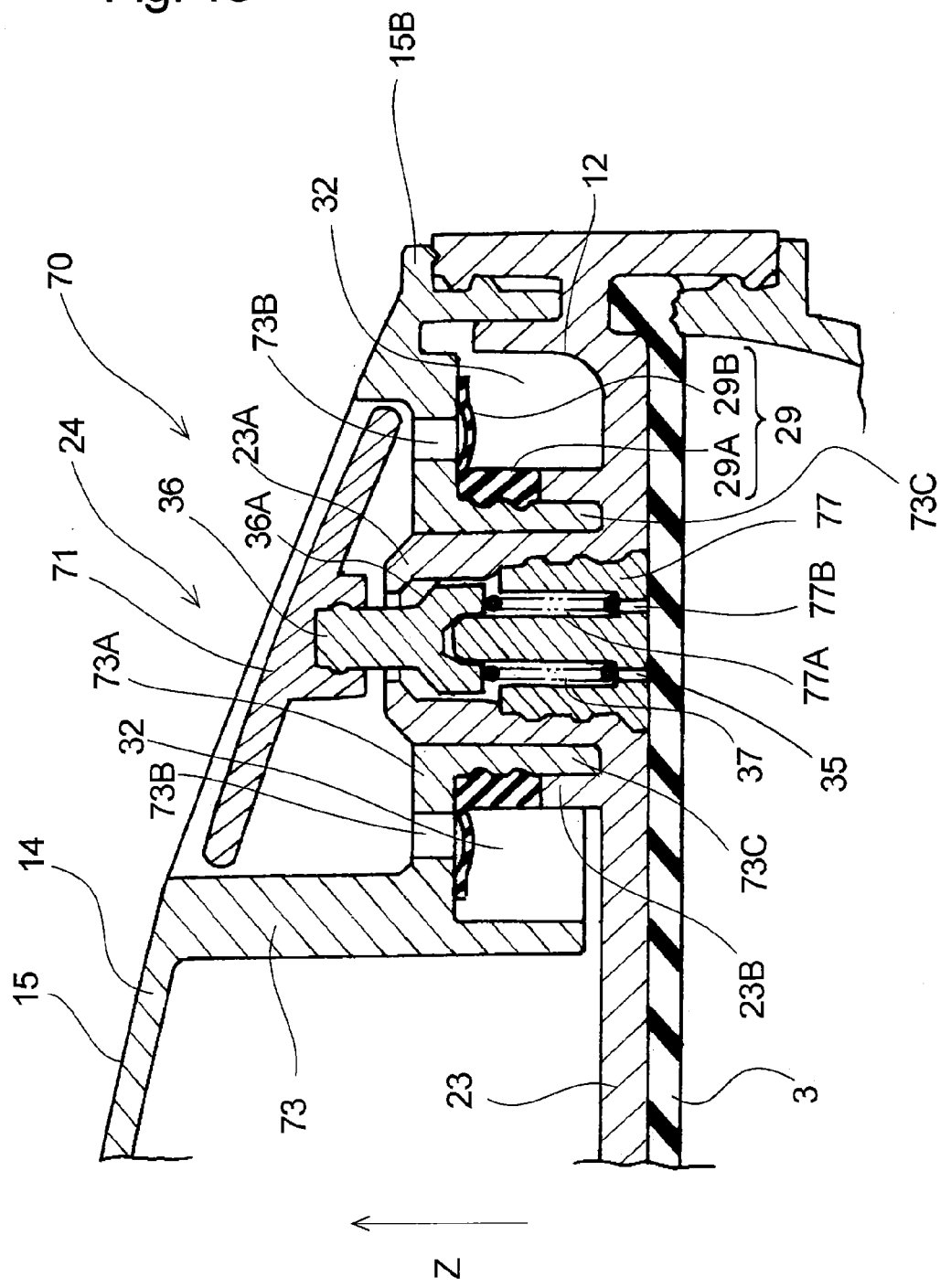
FIG. 15 is an enlarged sectional view of an integrated valve device illustrating a state that a space between a partition wall and an elastic body is communicated with the outside of a container as depressing a plug member.
Figure 16:
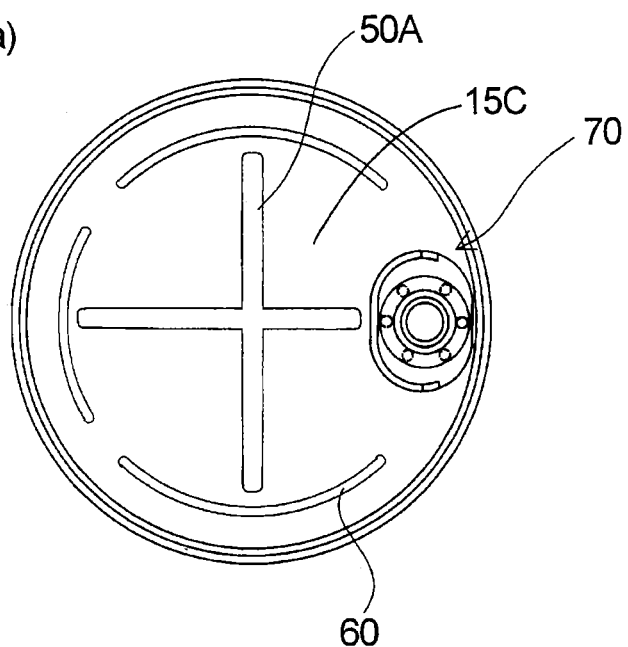
FIGS. 16(a) and 16(b) are views (corresponding to FIG. 10) illustrating arrangement of a reinforcement portion and a thin-walled portion of other embodiments of the present invention.
Figure 16:
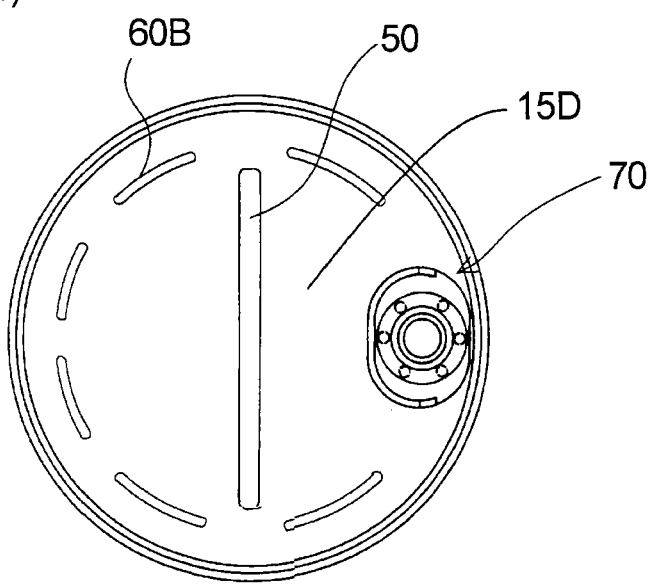

As illustrated in FIG. 15, the integrated valve device 70 includes an outer cylindrical wall 73 which is oval-shaped in plane view as being vertically arranged from the top face portion 14.

An opening hole wall portion 73A is arranged as being protruded from an inner circumferential face of the outer cylindrical wall 73. The opening hole wall portion 73A is a circular wall portion (see FIG. 10) having an oval-shaped outer circumferential edge and a circular inner circumferential edge and is a flat wall portion as being approximately in parallel to a plane passing through the circumferential edge 15B of the top face portion 14 (squeeze deformation portion 15). Six penetration holes 73B are formed at the opening hole wall portion 73A at intervals of 60° along the circular inner circumference (see FIG. 10). A cylindrical wall portion 73C is vertically arranged from the inner circumferential edge of the opening hole wall portion 73A. The second check valve 29 is attached to the cylindrical wall portion 73C. The second check valve 29 includes a cylindrical portion 29A which is concentric with the cylindrical wall portion 73C and a circular portion 29B which is arranged as being extended from an upper end of the cylindrical portion 29A to the outside in the radial direction (see FIG. 9). As illustrated in FIG. 15, the cylindrical portion 29A is fitted to an outer circumference of the cylindrical wall portion 73C. Further, the circular portion 29B covers a lower end of the penetration hole 73B as being abutted to the opening hole wall portion 73A.

In the present embodiment, the intake passage 32 is structured with spaces in the penetration holes 73B, spaces in the upper vicinities of the spaces, and spaces in the lower vicinities of the spaces. In a state that the squeeze deformation portion 15 is squeezed, the circular portion 29B of the second check valve 29 is intimately contacted to lower ends of the penetration holes 73B, so that the second check valve 29 closes the intake passage 32. When the squeezing is released, the circular portion 29B is separated from the penetration holes 73B, so that the second check valve 29 opens the intake passage 32.

The air-bleeding device 24 includes the coil spring 37 (elastic member), the plug member 36, and the communication passage 35 which provides communication between the inflation chamber 34 and the outside of the container 1' via the spring holding portion 77A (storage portion of the elastic member) which stores the coil spring 37 (elastic member). The plug member 36 closes the communication passage 35 as being urged by the coil spring 37 (elastic member) and opens the communication passage 35 at the time of being pressurized. In the present embodiment, the time when the plug member 36 is pressurized denotes time when force is applied to the plug member 36 in a direction to compress the coil spring (elastic member) 37 with a later-mentioned button member 71.

Here, the intake passage 32 which is opened and closed by the second check valve 29 surrounds the air-bleeding device 24. More specifically, in plane view of the squeeze container 1' viewing from the squeeze deformation portion 15 side, the communication passage 35 of the air-bleeding device 24 is surrounded by the penetration holes 73B being three or more which form the intake passage 32. The number of the penetration holes 73B which surround the communication passage 35 is preferably three or more, and more preferably, in a range between four and ten.

The communication passage 35 will be described in more detail. A cylindrical protrusion portion 23A is arranged as being protruding in the approximately-vertical direction from the partition wall 23 and a cylindrical outer protrusion 23B is arranged as being protruded at the same side of the cylindrical protrusion side 23A. That is, the outer protrusion 23B having lower height than the cylindrical protrusion portion 23A is raised from the partition wall 23 to surround the cylindrical protrusion portion 23A. The cylindrical wall portion 73C of the top face portion forming member 11 is fitted to a ring-shaped gap or a ring-shaped groove which is formed by the cylindrical protrusion portion 23A and the outer protrusion 23B. Further, the cylindrical portion 29A of the second check valve 29 is fitted so that an inner face thereof is contacted to an outer circumferential face of the cylindrical wall portion 73C and is sandwiched vertically by the outer protrusion 23B and the opening hole wall portion 73A. At such fitting and sandwiching, the respective members are maintained in an air-tight state therebetween.

A spring holding wall 77 which holds the coil spring 37 is fitted to a lower inner circumferential face of the cylindrical protrusion portion 23A.

As illustrated in FIG. 15 and the like, the partition wall 23 is not arranged at the inside of the cylindrical protrusion portion 23A. In a case that the inflation chamber 34 exists as being formed between the elastic body 3 and the partition wall 23, a lower end face of the spring holding wall 77 forms a part of an inner face of the inflation chamber 34. The spring holding portion 77A (storage portion of the elastic member) being an inner space which is shaped corresponding to the coil spring 37 and a plurality of hole portions 77B below the spring holding portion 77A are formed at the spring holding wall 77. Four of the hole portions 77B are arranged to provide communication between the spring holding portion 77A and the inside of the inflation chamber 34. In the present embodiment, the communication passage 35 which is opened and closed by the plug member 36 is structured with a space in the cylindrical protrusion portion 23A including the hole portions 77B and the spring holding portion 77A and a space at the upper vicinity of the cylindrical protrusion portion 23A.

As described above, in the present embodiment, the intake passage 32 including the plurality of penetration holes 73B surrounds the communication passage 35 which is structured with the space in the cylindrical protrusion portion 23A, so that the air-bleeding device 24 and the second check valve 29 are integrated.

Here, the upper inner circumferential face of the cylindrical protrusion portion 23A includes a taper portion which is tapered so that the inner side thereof becomes narrow toward the upper side as being formed at the upper end part of the cylindrical protrusion portion 23A and a non-taper portion which is approximately in parallel to z-direction as being continued to the lower end of the taper portion.

Further, the air-bleeding device 24 includes the button member 71 which is formed continuously to the plug member 36. As illustrated in FIG. 15, the button member 71 is a cover body covering the intake passage 32 which is structured with the space in the penetration holes 73B and spaces in the upper vicinities and lower vicinities of the space. As illustrated in FIGS. 7 and 8, the button member 71 is formed into a slightly curved plate shape. An outer face of the button member 71 is formed to have an arc sectional shape being flush with the outer face of the squeeze deformation portion 15 in a normal state (in a state that the button member 71 and the squeeze deformation portion 15 are not squeezed). Accordingly, as illustrated in FIG. 7, appearance of the container 1' provides a feeling of unity.

Further, as illustrated in FIG. 8, a gap between a circumferential edge of the button member 71 and the squeeze deformation portion 15 (top face portion 14) which surrounds the button member 71 is extremely small. Therefore, air passes therethrough but water, dust and the like hardly pass therethrough. Accordingly, foreign matters can be prevented almost perfectly from entering into the circular holes 73B owing to blockage with the button member 71.

The plug member 36 is continuously urged upward by the coil spring 37 having the lower end contacted to the coil spring 37. An inclined face 36A having a shape being matched to the abovementioned taper portion of the upper inner face of the cylindrical protrusion portion 23A is formed as a midpoint of the outer face of the plug member 36. As illustrated in FIG. 8, in a normal state (in a state that the button member 71 is not pressed), since the inclined face 36A of the outer face of the plug member 36 is urged upward as being intimately contacted to the taper portion of the upper inner face of the cylindrical protrusion portion 23A, the inner space of the cylindrical protrusion portion 23A is closed at the upper end part thereof and the communication passage 35 is closed.

Here, as illustrated in FIG. 15, when the button member 71 is downwardly pressed against urging force of the coil spring 37, the outer face of the plug member 36 is separated from the upper inner part of the cylindrical protrusion portion 23A. Accordingly, the communication passage 35 to provide communication between the outside of the container and the inside of the inflation chamber 34 is opened and air in the inflation chamber 34 is discharged to the outside through the communication passage 35. With the above, after content applying operation is completed, the swelled elastic body 3 can be easily returned into an original state illustrated in FIG. 8 with simple operation. Accordingly, the applying operation can be easily restarted. In addition, elastic restoration force of the elastic body 3 can be easily prevented from being lost owing to that the elastic body 3 is left in a swelled state.

According to the squeeze container 1' of the second embodiment (as well as a later-mentioned squeeze container 10 of a third embodiment), the sheet-shaped elastic body 3 can be gradually swelled to the storage portion 2 side by repeating squeezing of the squeeze deformation portion 15 and releasing thereof in a state that a content 33 which is liquid or gel is filled into the storage portion 2. Accordingly, an amount or speed of delivering the content can be arbitrarily controlled by appropriately controlling an amount or speed of swelling the elastic body 3.

Further, being different from the containers of Patent Literature 1 and Patent Literature 2, since the content 33 is squeezed and delivered by the sheet-shaped elastic body 3, it is possible to stably deliver an appropriate amount of content even when the content 33 becomes less. Here, in the squeeze container 1' of the present embodiment, the sheet-shaped elastic body 3 which has been plane-shaped at the beginning can be swelled until becoming to a solid shape (solid shape being like a slightly irregular hemisphere) along the shape of the inner face of the storage portion 2.

Here, storing and filling of the content 33 into the storage portion 2 may be performed with the cover body 7 detached or via the delivery passage 5 without detaching the cover body 7.

Further, the squeeze deformation portion 15 includes the linear reinforcement portion 50 which traverses the apex portion 15A and the linear thin-walled portion 60 which is formed in the direction along the circumferential edge 15B. Accordingly, even if the squeeze container 1' of the present embodiment is not made of material which is specifically selected, the squeezed deformation portion 15 is easily deformed by being squeezed and is easily returned from a deformed state into an original state when the squeezing is released. In addition, a swell amount of the elastic body 3 with one squeezing can be adjusted in accordance with a forming position of the thin-walled portion 60.

Further, since the thin-walled portion 60 is formed like discontinued lines in the squeeze container 1', strength at forming positions of the thin-walled portion 60 can be ensured.

Further, in the squeeze container 1' (as well as the later-mentioned squeeze container 10 of the third embodiment), the air-bleeding device 24 and the second check valve 29 are integrated so that the intake passage 32 which is opened and closed by the second check valve 29 surrounds the communication passage 35 of the air-bleeding device 24. Accordingly, area of the squeeze deformation portion 15 (i.e., section capable of receiving squeezing operation) at the top face portion 14 is widened compared to a case that the air-bleeding device 24 and the second check valve 29 are arranged at different positions at the top face portion 14. Accordingly, compared to a case that the air-bleeding device 24 and the second check valve 29 are arranged at different positions, the squeeze container 1' of the present embodiment has higher flexibility for a section to be squeezed and higher operability of content delivering operation. Further, owing to integration of the air-bleeding device 24 and the second check valve 29, the squeeze container 1' has superior appearance as compactly arranging members which are exposed to the outside.

Further, in the air-bleeding device 24 of the present embodiment, since the coil spring 37 which performs urging to close the communication passage 35 is stored in the spring holding portion 77A (storage portion of the elastic member) which forms a part of the communication passage 35, space-saving of the air-bleeding device 24 can be further achieved Further, in the air-bleeding device 24 of the squeeze container 1' of the present embodiment including the button member 71 which is arranged continuously to the plug member 36, the plug member 36 opens the communication passage 35 against urging of the coil spring 37 when the button member 71 is pressed with a hand. Further, the button member 71 is a cover body which covers the upper side of the intake passage 32. Accordingly, foreign matters can be prevented from entering to the intake passage 32 and design can be improved as enhancing a feeling of unity of appearance with the squeeze deformation portion 15. Further, it is preferable in a viewpoint of parts count reduction due to doubling as the cover body and the button member having the above functions.

Further, in the squeeze container 1' of the present embodiment, since the outer face shape of the button member 71 is matched to the outer face shape of the squeeze deformation portion 15, the squeeze container 1' has a better feeling of unity and the design thereof is improved.

Here, the gap between the button member 71 and the squeeze deformation portion 15 (top face portion 14) is preferably in a range between 0.01 mm and 5 mm, and more preferably, in a range between 0.05 mm and 1 mm.

Further, in the squeeze container 1' of the present embodiment, the pressurization means 4 includes the pressurization chamber 22 of which inner volume is decreased with deformation of the squeeze deformation portion 15 and the partition wall 23 which is arranged between the pressurization chamber 22 and the elastic body 3. The intake passage 32 of the second check valve 29 provides communication between the inside of the pressurization chamber 22 and the outside of the container. The communication passage 35 of the air-bleeding device 24 provides communication between the outside of the container and the inside of the inflation chamber 34 which is formed between the partition wall 23 and the elastic body 3. That is, the air-bleeding device 24 and the second check valve 29 which are integrated adopts an innovative mechanism to achieve integration of the intake passage 32 and the communication passage 35 being two air passages which provide communication respectively to separate spaces in the container.

As described above, in the squeeze container 1', the air-bleeding device 24 and the second check valve 29 are integrated so that the intake passage 32 which is opened and closed by the second check valve 29 surrounds the communication passage 35 of the air-bleeding device 24. Therefore, the area of the squeeze deformation portion 15 at the top face portion 14 is wider compared to a case that the air-bleeding device 24 and the second check valve 29 are arranged at different positions. In the squeeze container 1' of the present embodiment, the wider area causes delay of elastic restoration of the squeeze deformation portion 15 after squeezing is released compared to a case that the air-bleeding device 24 and the second check valve 29 are arranged at different positions. Arranging the reinforcement portion 50 causes acceleration of the elastic restoration. That is, the effect of the reinforcement portion 50 becomes larger in the present embodiment.

The reinforcement portion and/or the thin-walled portion may not be arranged in the inventions other than the second invention.

Further, even in a case of arranging the reinforcement portion and/or the thin-walled portion, the way of arranging thereof may be appropriately modified.

For example, the reinforcement portion may not be formed like a single line. A reinforcement portion 50A of a squeeze deformation portion 15C illustrated in FIG. 16(a) is formed of two lines which are approximately orthogonal. It is considered that the above further facilitates restoration of the squeeze deformation portion 15C from the deformation.

Further, the thin-walled portion is not limited to a shape of three arcs as the abovementioned squeeze container 1'. A squeeze deformation portion 15D illustrated in FIG. 16(b) includes a thin-walled portion 60B which is formed into a shape of lines as being broken more finely. In this manner, lengths of the thin-walled portion 60B may not be constant and intervals thereof may not be constant as well.

Further, for example, the air-bleeding device 24 and the second check valve 29 are not necessarily required to be integrated so that the intake passage 32 surrounds the communication passage 35. As a squeeze container 1A illustrated in FIG. 17, it is also possible to arrange the air-bleeding device 24 to the other end side of the top face portion 14 against a position where the second check valve 29 is arranged. In this case, when the reinforcement portion 50 is arranged to intersect to a straight line connecting the air-bleeding device 24 and the second check valve in plane view, the squeeze deformation portion can be returned from the deformed state more easily.

Figure 18:
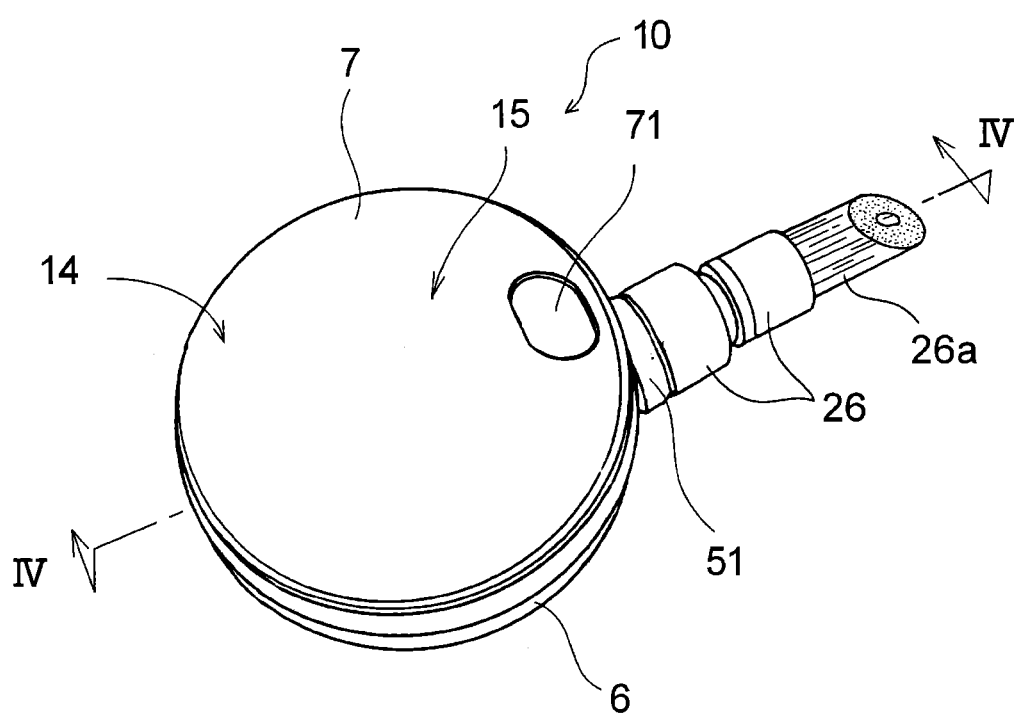
FIG. 18 is a perspective view illustrating a third embodiment of a squeeze container of the present inventions (first to sixth inventions).
Figure 20:
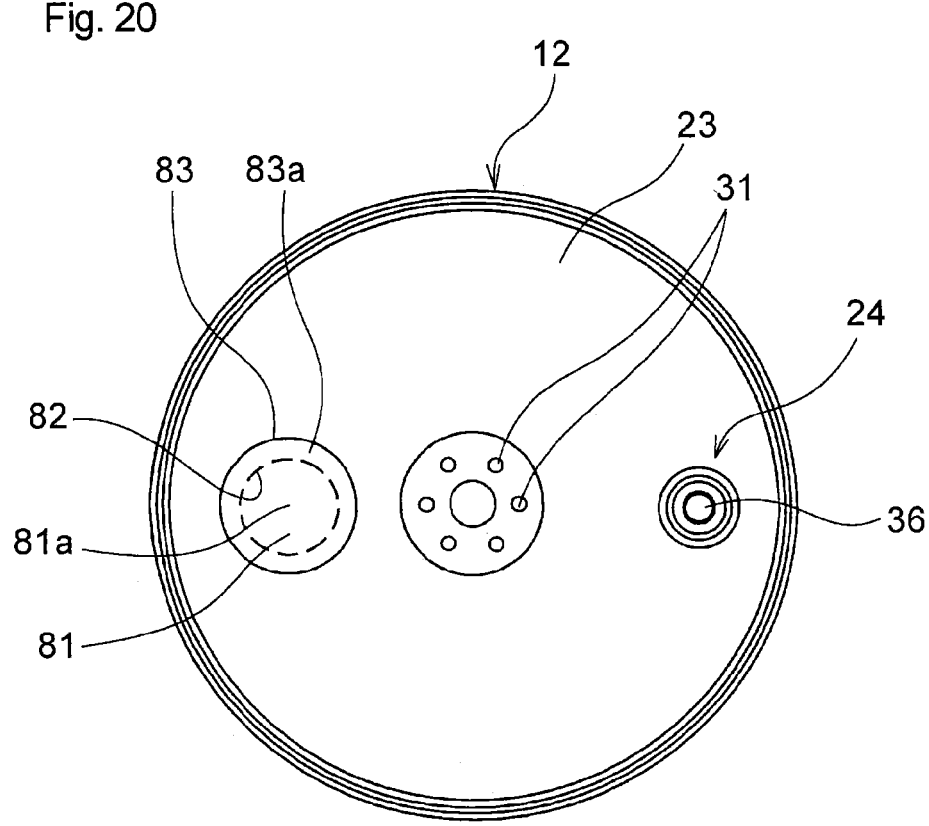
FIG. 20 is a plane view of a partition wall of the container illustrated in FIG. 18 viewing from a pressurization chamber side.

Next, fifth and sixth inventions will be described based on a squeeze container 10 of the third embodiment illustrated in FIGS. 18 and 19. The squeeze container 10 of the third embodiment is also an embodiment of any of the first to third, fifth and sixth inventions.

Figure 19:
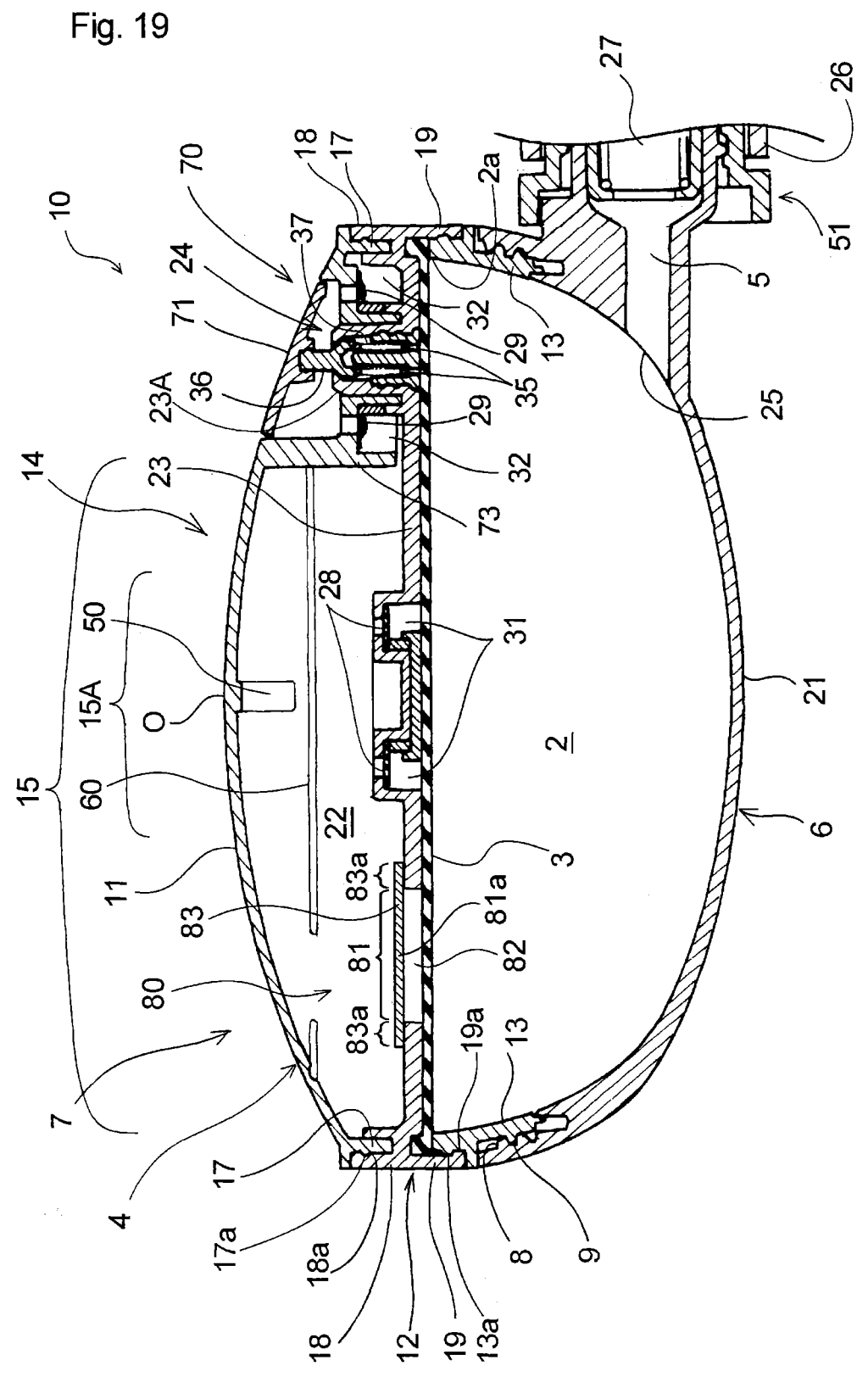
Figure 21:
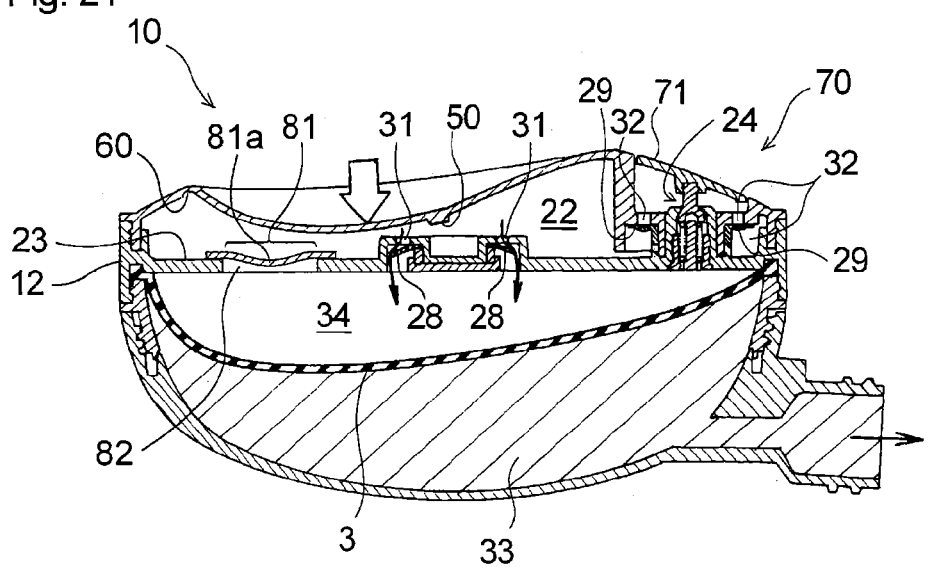
FIG. 21 is a sectional view illustrating a squeeze-deformed state of a squeeze deformation portion of the squeeze container of FIG. 18.
Figure 22:
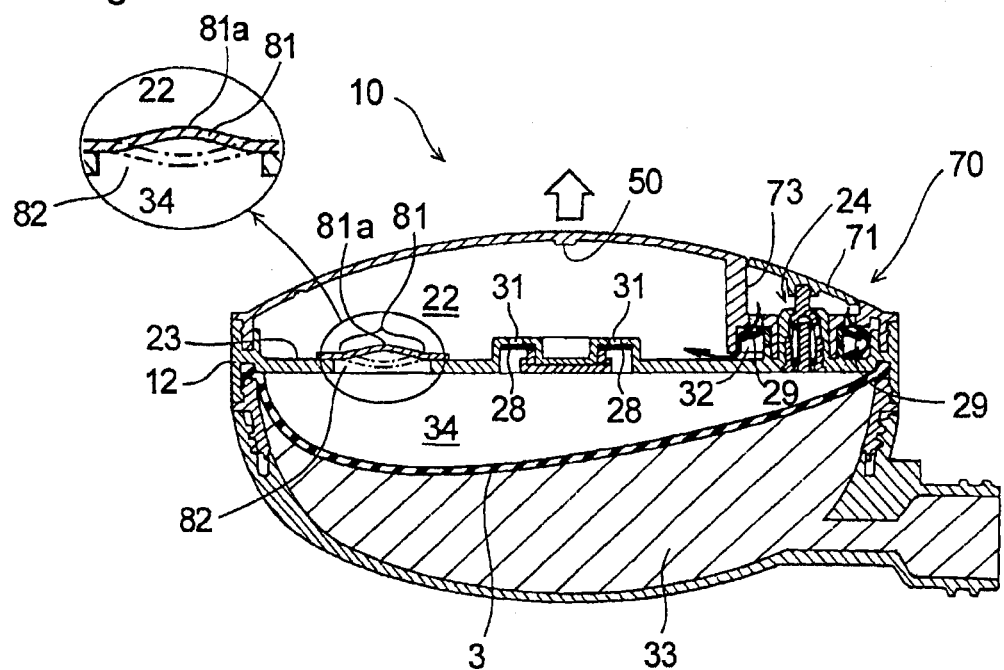
FIG. 22 is a sectional view illustrating a state that the squeeze deformation portion of the squeeze container of FIG. 18 is returned from a deformed state into an original state.

As illustrated in FIGS. 19, 21 and 22, the squeeze container 10 of the third embodiment of the present invention includes a storage portion 2 in which a content 33 is stored and which has a delivery passage 5 to provide communication between the inside and outside thereof, an inflation chamber 34 and pressurization means 4. Here, owing to that the pressurization means 4 fills gas to the inflation chamber 34, volume of the inflation chamber 34 is increased. Then, owing to that the volume of the inflation chamber 34 is increased, a content 33 in the storage portion 2 is delivered to the outside of the storage portion 2 via the delivery passage 5. The inflation chamber 34 has a part thereof structured with an elastic body 3 and the volume thereof is increased with deformation of the elastic body while gas is filled into the inflation chamber 34 by the pressurization means 4. Further, the squeeze container 10 includes an inflation absorbing portion which decreases the volume of the inflation chamber 34 at the time when gas-filling into the inflation chamber 34 by the pressurization means 4 is completed.

The storage portion 2 in which a content is stored has an approximately-circular opening portion 2a at an upper face thereof as being concaved, that is, as being concaved to be a hemispherical or partially-spherical shape. The elastic body 3 is formed like an approximately-circular sheet and is arranged on the storage portion 2 to cover the whole opening portion 2a. Here, the storage portion of the present invention may have larger sectional area at the inside thereof than area at the opening portion.

The pressurization means 4 includes an approximately-circular flat-plate-shaped partition wall 23 of which one face is covered with the elastic body 3, a dome-shaped squeeze deformation portion 15, and a first check valve 28. The inflation chamber 34 is a space between the partition wall 23 and the sheet-shaped elastic body 3.

The squeeze deformation portion 15 is deformed with a squeeze force which is applied by a hand toward the partition wall 23 from a side opposite to the partition wall 23 and is returned into an original state, that is, a state before squeezing, by releasing of the squeezing. A pressurization chamber 22 being a small room of which inner volume is decreased with deformation of the squeeze deformation portion 15 is formed as being surrounded by the squeeze deformation portion 15 and the partition wall 23. Then, the partition wall 23 performs partitioning between the pressurization chamber 22 and the sheet-shaped elastic body 3. A communication passage 31 which connects the inflation chamber 34 and the pressurization chamber 22 is arranged at the partition wall 23.

The first check valve 28 is arranged at the communication passage 31. The first check valve 28 allows only ventilation toward the inflation chamber 34 from the squeeze deformation portion 15 side, that is, the pressurization chamber 22, and substantially prohibits movement of air in the inflation chamber 34 to the pressurization chamber 22. The pressurization means 4 increases the volume of the inflation chamber 34 (swells the elastic body 3 to the storage portion 2 side with gas pressure) by feeding gas in the pressurization chamber 22 to the inflation chamber 34 via the communication passage 31 when the squeeze deformation portion 15 is squeezed.

Further, the inflation chamber 34 of the present embodiment is a space between the partition wall 23 and the elastic body 3. In an initial state before squeezing the squeeze deformation portion 15, there does not exist a space being anything like a chamber between the partition wall 23 and the sheet-shaped elastic body 3 as the both being intimately contacted. However, the inflation chamber in the present application includes this space between the partition wall 23 and the sheet-shaped elastic body 3 which are in an intimately contacted state. Here, it is also possible that a gap or a space having predetermined volume exists between the partition wall 23 and the elastic body 3 from the initial state before squeezing the squeeze deformation portion 15.

Further, the partition wall 23 includes a pressure relief portion 80 which eliminates residual pressure as decreasing pressure in the inflation chamber 34 when squeezing of the squeeze deformation chamber 15 is released. The pressure relief portion 80 includes a displacement portion 81 having at least a part to be moved (displaced) toward the pressurization chamber 22 side when squeezing of the squeeze deformation portion 15 is released.

In the following, the squeeze container 10 of the third embodiment will be described more specifically.

The squeeze container 10 of the third embodiment has the similar structure to that of the squeeze container 1 of the second embodiment except for that the pressure relief portion 80 is arranged at the partition wall 23. Accordingly, the third embodiment will be described mainly on points which are different from the second embodiment while description on similar points will be skipped as providing the same numerals to FIGS. 18 to 22 and the like. Here, FIGS. 9 to 11, 14 and 15 are applied similarly to the squeeze container 10 of the third embodiment.

A partition wall forming member 12 forms a plane-shaped partition wall 23 which is circular in plane view between the pressurization chamber 22 and the sheet-shaped elastic body 3. The partition wall 23 performs air-tight partitioning between the pressurization chamber 22 and the sheet-shaped elastic body 3.

The squeeze container 10 of the third embodiment includes the pressure relief portion 80 at the partition wall 23. The pressure relief portion 80 includes the displacement portion 81 having at least a center portion 81a to be displaced when squeezing of the squeeze deformation portion 15 is released. As illustrated in FIG. 22, at least a part of the displacement portion 81, specifically, the center portion 81a, is moved toward the pressurization chamber 22 side when squeezing of the squeeze deformation portion 15 is released. Accordingly, inner volume (volume) of the pressurization chamber 22 is decreased. As a result, pressure in the inflation chamber 34 is decreased.

The pressure relief portion 80 of the present embodiment will be described more specifically. As illustrated in FIG. 19, the pressure relief portion 80 includes a penetration hole 82 being circular in plane view which is formed at the partition wall forming member 12 and a flexible member 83 which is arranged to cover the penetration hole 82. The pressure relief portion 80 is also thought of corresponding to the inflation absorbing portion.

The flexible member 83 is shaped like a thin plate or a sheet, has flexibility, and is made of non-air-permeable material. In the flexible member 83, a circumferential edge portion 83a thereof is air-tightly fixed to a periphery of the penetration hole 82 with an arbitrary fixing method such as welding and bonding.

The displacement portion 81 of the present embodiment is a center section (section other than the circumferential edge portion 83a) of the flexible member which is not fixed to the partition wall forming member 12. When squeezing of the squeeze deformation portion 15 is released, the displacement portion 81 has at least the center portion 81 moved from a position under a state that the squeeze deformation portion is squeezed as illustrated in FIG. 21 toward the pressurization chamber 22 side as illustrated in FIG. 22. Here, since the movement of the displacement portion 81 is displacement caused by deformation of the flexible member 83 having flexibility, the displacement portion 81 of the present embodiment also corresponds to a flexible portion of the present invention.

When the container 10 is in a non-usage state, in particular, when there is no pressure difference between the pressurization chamber 22 and a space at the elastic body 3 side from the partition wall 23, the displacement portion 81 of the present embodiment is formed like an approximate plane shape, as illustrated in FIG. 19. While air in the pressurization chamber 22 is fed to the space between the partition wall 23 and the elastic body 3 as squeezing the squeeze deformation portion 15, pressure in the pressurization chamber 2 is larger than pressure in the pressurization chamber 34. Accordingly, the displacement portion 81 has a shape like a curved convex face as protruding toward the elastic body 3 side, as illustrated in FIG. 21. On the other hand, when the squeezing of the squeeze deformation portion 15 is released thereafter, the squeeze deformation portion 15 starts to be returned into an original state and the pressure in the pressurization chamber 22 is rapidly decreased. Then, the pressure in the pressurization chamber 22 becomes lower than the pressure in the inflation chamber 34 and the displacement portion 81 is varied into a shape like a curved convex face as protruding toward the pressurization chamber 22 side (opposite side to the elastic body 3), as illustrated in FIG. 22. The variation in shape of the displacement portion 81 occurs within a period until the squeeze deformation portion 15 becomes in a state before the squeezing illustrated in FIG. 22 from the deformed state illustrated in FIG. 21. The variation in shape of the flexible member 83 is minute compared to variation in shape of the squeeze deformation portion, as illustrated in FIGS. 21 and 22.

In the squeeze container 10 of the present embodiment, the pressure relief portion 80 having the above structure is arranged at the partition wall 23. Accordingly, when squeezing is released after a content 33 is delivered as squeezing the squeeze deformation portion 15, inner volume (volume) of a space surrounded by the partition wall 23, the elastic body 3 and the flexible member 83 is instantaneously increased by the amount of deformation of the displacement portion 81. Subsequently, inflation of the elastic body 3 is stopped and the elastic body 3 is slightly moved to the partition wall 23 side owing to shrinkage, so that the inner volume (volume) of the inflation chamber 34 is decreased. Accordingly, the air pressure in the inflation chamber 34 between the partition wall 23 and the elastic body 3 is instantaneously decreased, and simultaneously, pressure force (force to press the elastic body) acting in a direction to swell the elastic body 33 is instantaneously decreased.

Therefore, inflation of the elastic body 3 is stopped almost simultaneously with releasing of squeezing of the squeeze deformation portion and delivery of the content 33 is stopped almost simultaneously therewith.

Here, the inner volume (volume) of the inflation chamber 34 denotes inner volume (volume) of a space formed by an inner face of the elastic body 3 and a plane including an inner face of the partition wall 23, and is varied directly with displacement of the elastic body 3. However, the volume is not varied directly with displacement of the displacement portion 81.

As described above, according to the squeeze container 10 of the third embodiment, delivery of the content 33 can be promptly stopped by releasing squeezing of the squeeze deformation portion 15. In addition, delivery of the content 33 in the container 10 can be rapidly performed by squeezing and deforming the squeeze deformation portion 15. Accordingly, a user can easily perform delivering of the content 33 and stopping of the delivering without causing a feeling of strangeness at response speed corresponding to the will of the user.

In the light of prompt stopping of content delivery, area of the displacement portion 81, in other words, area of a deformable section of the flexible member 83 (being the same as area of the penetration hole 82 in the present embodiment) is preferably in a range between 0.4% and 50% of the total area of the partition wall 23 (area including the penetration hole 82), and more preferably, in a range between 1% and 25%. Here, the area of the displacement portion 81 denotes area measured in a state that the displacement portion and the partition wall are made to be planar as illustrated in FIG. 19 or flat area of the respective portions as being projected in a perpendicular direction to the partition wall 23.

Further, it is preferable that the maximum variation amount of the volume in the inflation chamber 34 due to variation in shape of the displacement portion 81 (a value acquired on the assumption that the elastic body 3 is not deformed at all) is 10% or less of the volume of the storage portion 2 (value which is not varied in accordance with positions of the elastic body 3).

Here, although the displacement portion 81 is not necessarily required to be an elastic body with elasticity, it is preferable that the displacement portion 81 is softer than sections of the partition wall 23 other than the displacement portion 81. Examples of a method to soften the displacement portion 81 include a method (1) to adopt forming material of the flexible member 83 which forms the displacement portion 81 being softer than forming material of the other sections of the partition wall 23, a method (2) to thin thickness of the displacement portion 81 or the flexible member 83 which forms the displacement portion 81 compared to thickness of the other sections of the partition wall 23, and a method (3) of combination of the above.

Examples of the method (1) include a method that the flexible member 83 is made of polyethylene and the other sections of the partition wall 23 are made of polypropylene. Examples of the method (2) include a method that the thickness of the displacement portion 81 or the flexible member 83 which forms the displacement portion 81 is set to be in a range of $1/5$ and $1/100$ of the thickness of the other sections of the partition wall 23.

The thickness of the displacement portion 81 or the flexible member 83 which forms the displacement portion 81 is not specifically limited as long as being capable of forming the displacement portion. An example in a case of being formed of synthetic resin is in the order of 0.1 mm to 2 mm.

The sheet-shaped elastic body 3 of the third embodiment is also arranged along the partition wall 23 as being closed to the partition wall 23. Further, the sheet-shaped elastic body 3 is fixed as a peripheral part thereof being sandwiched at a space between the partition wall forming member 12 and the elastic body fixing member 13. The sheet-shaped elastic body 3 is not fixed to the partition wall forming member 12 other than the peripheral part. Accordingly, as illustrated in FIG. 21, the sheet-shaped elastic body 3 can be swelled to the storage portion 2 side with pressure (air pressure) of air fed from the pressurization means 4.

A nozzle member 26 is fixed to the delivery passage 5 of the third embodiment as well in a detachably attachable manner as being similar to the second embodiment (see FIGS. 13 and 14). A filling-delivering portion 51 has a flow passage of fluid at the inside thereof. The filling-delivering portion 51 opens the flow passage in a state that the nozzle member 26 is attached and closes the flow passage in a state that the nozzle member 26 is not attached.

Description for the second embodiment is also applied to the third embodiment for a structure of the filling-delivering portion 51, a structure of the nozzle member 26, a method for fixing the nozzle member to the filling-delivering portion 51, a method for storing and filling the content 33 into the storage portion 2, and the like.

According to the squeeze container 10 of the third embodiment, since the pressure relief portion 80 having the abovementioned structure is arranged at the partition wall 23, inflation of the elastic body 3 is stopped almost simultaneously with releasing of squeezing of the squeeze deformation portion 15 and delivery of the content 33 is stopped almost simultaneously therewith. Accordingly, a user can easily perform delivering of the content 33 due to squeezing of the elastic body 3 and stopping of the delivery without causing a feeling of strangeness.

In addition, stopping of the delivering of the content 33 can be performed by releasing squeezing of the squeeze deformation portion 15, that is, only by weakening the force applied to the squeeze deformation portion 15 to the degree that the squeeze deformation portion 15 starts to be returned into an original state. Accordingly, it is possible to perform delivering due to squeezing of the elastic body 3 and stopping of the delivering as a user likes.

The squeeze container according to the fifth and sixth inventions is applicable as a squeeze container for liquid having relatively high viscosity.

Not limited to the abovementioned embodiment, the fifth invention may be appropriately modified.

Figure 23:
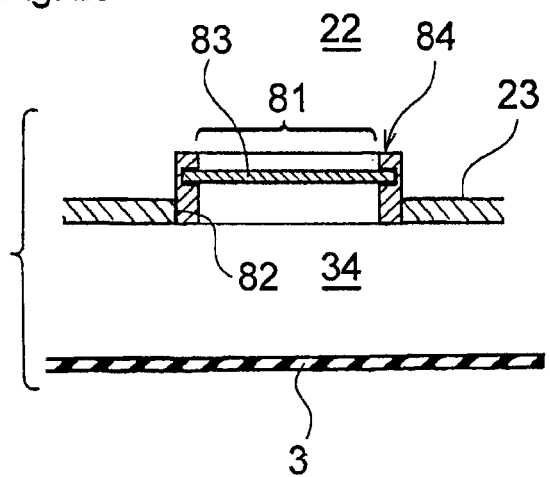
FIG. 23 is a view illustrating a pressure relief portion (inflation absorbing portion) of another embodiment of the fifth invention.

For example, instead of directly joining the flexible member 83 to the periphery of the penetration hole 82 of the partition wall forming member 12 as in the abovementioned third embodiment, the flexible member 83 may be fixed to the partition wall forming member 12 via a support body which supports the circumferential edge portion thereof. Specifically, as an embodiment illustrated in FIG. 23, it is also possible that the periphery of the flexible member 83 is fixed into a groove of an inner circumferential face of a frame-shaped support body 84 and that the support body 84 is fixed to the periphery of the penetration hole 82 of the partition wall forming member 12.

Further, the pressure relief portion (inflation absorbing portion) of the present invention may include a movable member 85 which is displaced as a whole toward the pressurization chamber 22 side when squeezing of the squeeze deformation portion 15 is released. The movable member 85 of a pressure relief portion 80A of an embodiment illustrated in FIG. 24 has a shape that a periphery of a disc is connected to an inner face of a cylindrical body at a center part in the axial length direction. The movable member 85 is formed of non-porous material and is fixed to the penetration hole 82 of the partition wall forming member 12 in a state of being stored in a closed-end cylindrical holding body 86 having a penetration hole at the bottom portion thereof. An upper end of the holding body 86 is closed with a cover body 87 having a penetration hole, so that the movable member 85 is prevented from exiting from the inside of the holding body 86. An oil solution to improve air-tightness is interposed at a boundary face between an outer circumferential face of the movable member 85 and an inner circumferential face of the holding body 86.

In a case of arranging the abovementioned pressure relief portion 80A as well, pressure in the inflation chamber 34 (see FIG. 22) formed between the partition wall 23 and the elastic body 3 is instantaneously decreased as the movable member 85 being displaced toward the pressurization chamber 22 side when squeezing is released after the squeeze deformation portion 15 is squeezed. Accordingly, delivery of the content 33 can be stopped almost simultaneously with releasing of squeezing of the squeeze deformation portion 15.

The displacement portion and the flexible portion of the present invention may be shaped like a flat face while air in the pressurization chamber 22 is fed into a space between the partition wall 23 and the elastic body 3 with squeezing of the squeeze deformation portion 15 while being varied into a shape like a curved convex face convexed toward the pressurization chamber 22 side when squeezing of the squeeze deformation portion 15 is released.

Figure 25:
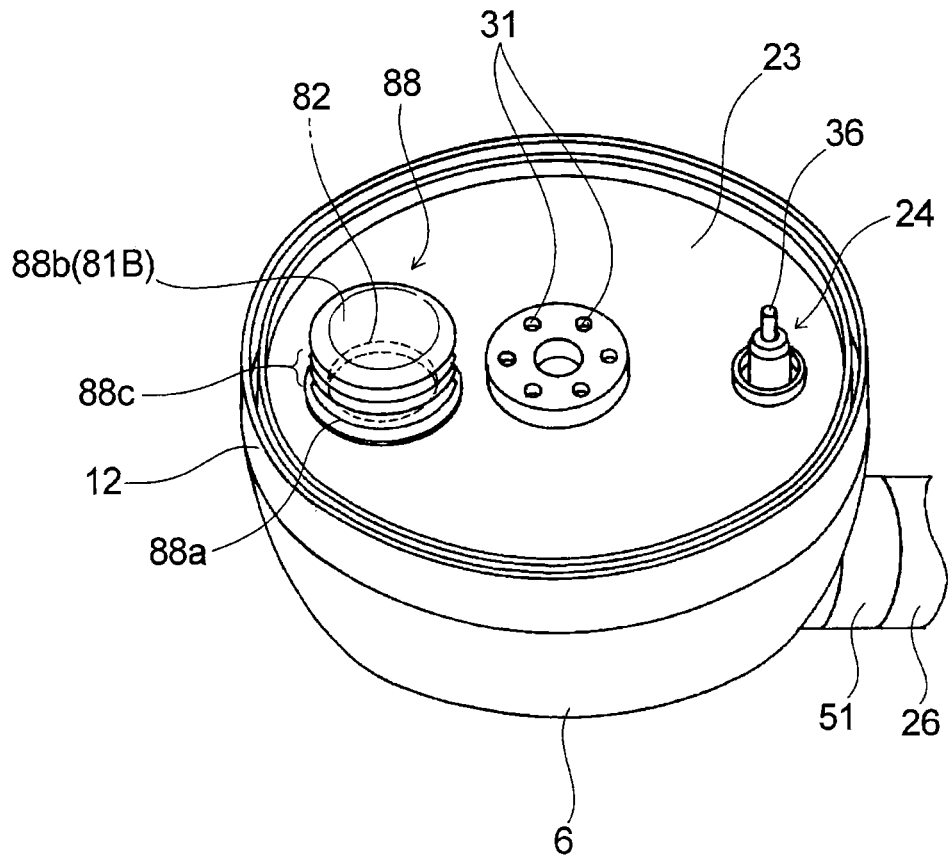
FIG. 25 is a perspective view illustrating a container of still another embodiment of the fifth invention in a state that a top face portion forming member is detached.

The displacement portion of the present invention adopts a bellows-shaped elastic body 88 as illustrated in FIG. 25.

That is, the pressure relief portion (inflation absorbing portion) can be structured by utilizing a bellows-shaped elastic body of which one end is closed. More specifically, as illustrated in FIG. 25, a pressure relief portion 80 of another embodiment of the fifth invention includes a penetration hole 82 being circular in plane view which is formed at the partition wall forming member 12 (partition wall 23) and the bellows-shaped elastic body 88 which is arranged at the partition wall 23 at the squeeze deformation portion 15 side to cover the penetration hole 82.

The bellows-shaped elastic body 88 is made of non-porous material having elasticity, for example, polyolefin resin such as polyethylene. An uncovered one end 88*a* of the bellows-shaped elastic body 88 is air-tightly fixed to the periphery of the penetration hole 82 with an arbitrary fixing method such as welding and bonding.

Figure 26:
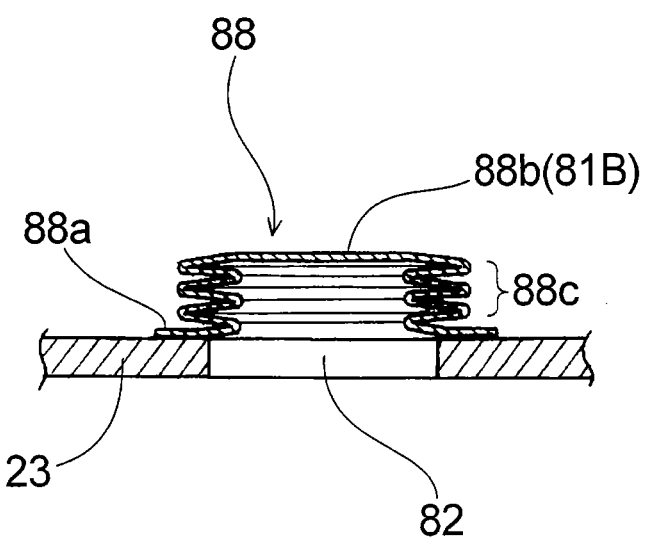
FIG. 26 is a sectional view illustrating the pressure relief portion (inflation absorbing portion) of the same embodiment as FIG. 25 when the squeeze deformation portion is squeeze-deformed.
Figure 27:
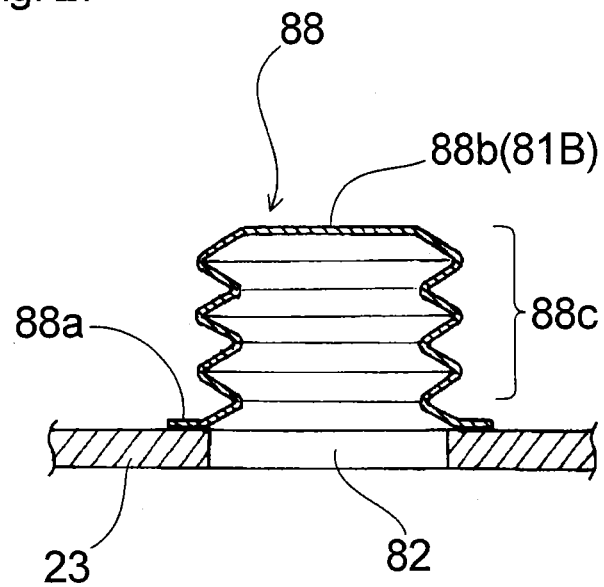
FIG. 27 is a sectional view illustrating the pressure relief portion (inflation absorbing portion) of the same embodiment as FIG. 25 when squeezing of the squeeze deformation portion is released.

A displacement portion 81B of the present embodiment is a covered side (specifically, a covered end) 88*b* of the bellows-shaped elastic body 88. When squeezing of the squeeze deformation portion 15 is released, the displacement portion 81B is moved from a position under a state that the squeeze deformation portion 15 is squeezed as illustrated in FIG. 26 toward the pressurization chamber 22 side (opposite side to the elastic body 3) as illustrated in FIG. 27. Here, since the movement of the displacement portion 81B is displacement caused by deformation of a bellows portion 88*c* of the bellows-shaped elastic body 88, the bellows portion 88*c* of the present embodiment also corresponds to the flexible portion of the present invention.

In the abovementioned containers 1', 10, the air-bleeding device 24 and the second check valve 29 are integrated while the intake passage 32 including the plurality of penetration holes 73B surrounds the communication passage 35 which is formed of a space in the cylindrical protrusion portion 23A. Here, instead of the above, it is also possible that a hole structuring the intake passage is formed as a single circular hole and that the communication passage 35 of the air-bleeding device 24 is surrounded by the hole.

Figure 24:
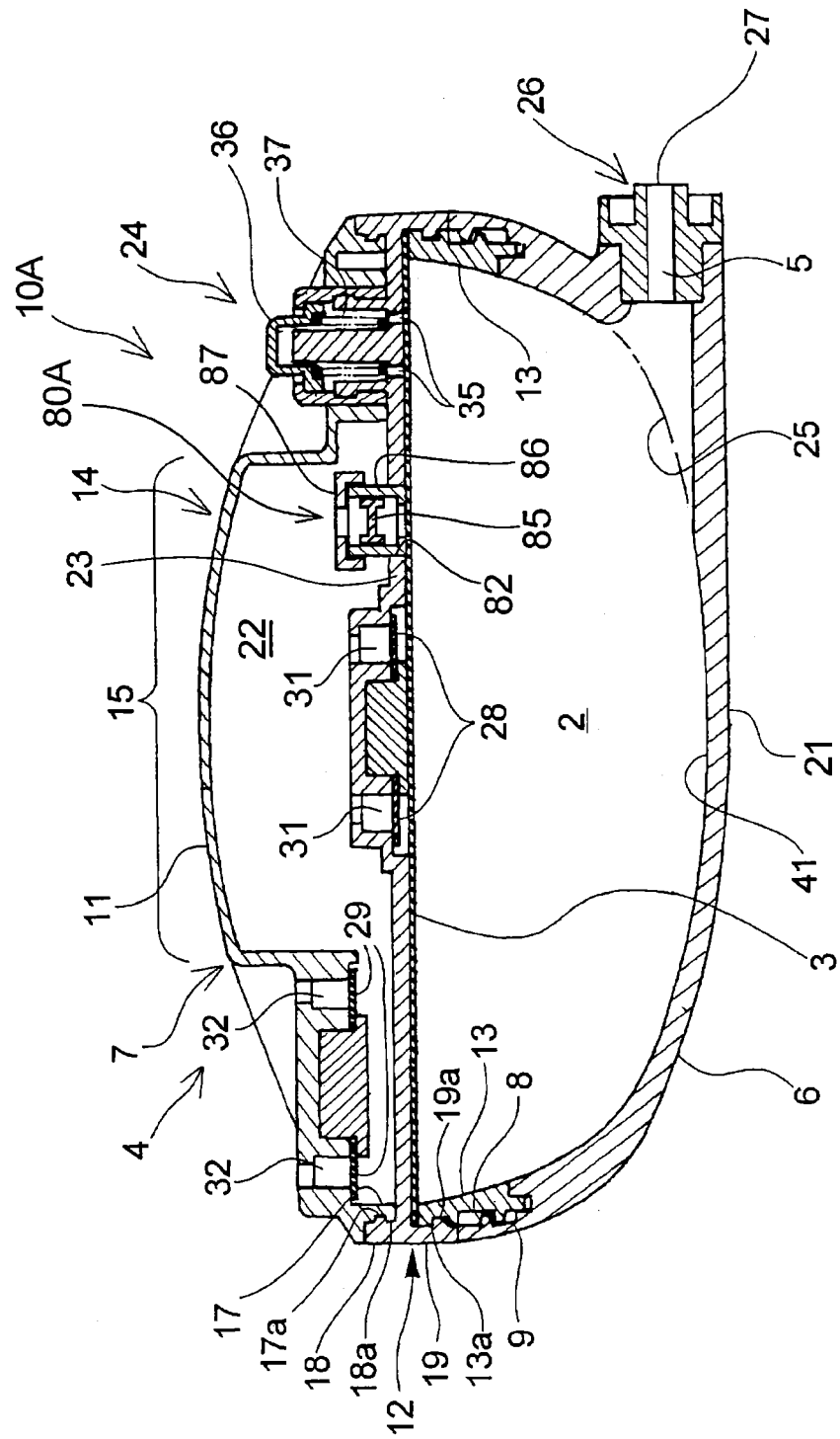
FIG. 24 is a sectional view (corresponding to FIG. 19) illustrating still another embodiment of the fifth invention.

Further, as illustrated in FIG. 24, the air-bleeding device 24 and the second check valve 29 may be arranged separately at different positions of the top face portion 14.

Further, it is possible to eliminate either or both of the reinforcement portion 50 and the thin-walled portion 60 of the squeeze deformation portion 15.

Next, seventh and eighth inventions will be described with reference to FIGS. 28 to 37.

Figure 34:
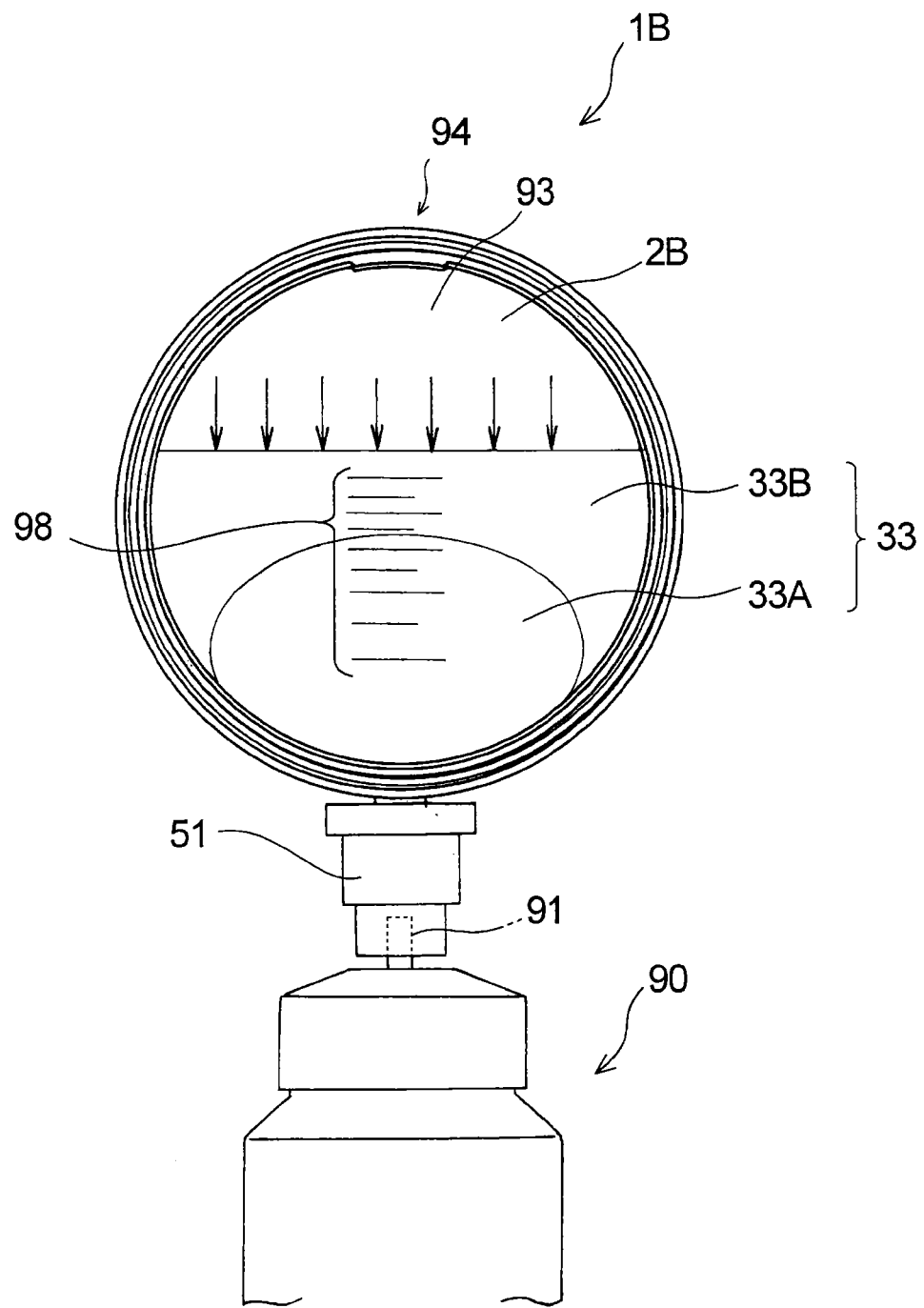
FIG. 34 is a schematic view illustrating a state that liquid 33A is filled into the container of FIG. 28 by an aerosol container after filling liquid 33B.

In an embodiment of a method of filling liquid of the present invention (seventh invention), liquid 33A discharged from an aerosol container 90 is filled into a container 1B including a liquid storage portion 2B with which an amount of the filled liquid 33 is visible from the outside, as illustrated in FIG. 34. Further, before filling of the liquid 33A to be filled by the aerosol container 90, second liquid 33B having lower viscosity than the liquid 33A is filled into the liquid storage portion 2B with an arbitrary method.

As illustrated in FIG. 34, the container 1B being an embodiment of a container of the present invention (eighth invention) is a container into which the liquid 33A is filled by the aerosol container 90 and is provided with the liquid storage portion 2B with which an amount of the filled liquid 33A, 33B is visible from the outside. In FIG. 34, a scale 98 enables to accurately measure an amount of the liquid 33A and/or 33B as being arranged at a container body 6 which is made of transparent plastic.

Figure 33:
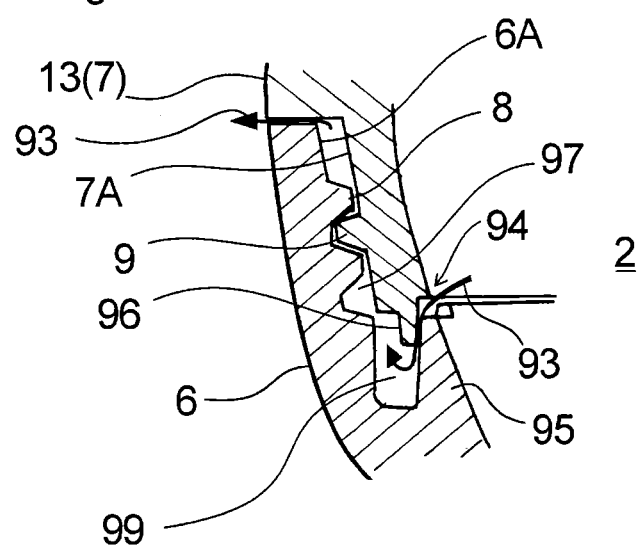
FIG. 33 is an enlarged view of a section surrounded by circle P in FIG. 29.

Further, as illustrated in FIG. 33, the liquid storage portion 2B is provided with a discharge passage 94 capable of discharging air 93 in the liquid storage portion 2B at the time of filling the liquid 33A with the aerosol container 90. The discharge passage 94 is formed to increase air pressure in the liquid storage portion 2B owing to filling of the liquid 33A and to maintain the positive pressure state during the filling of the liquid 33A while preventing the liquid 33 in the liquid storage portion 2B from leaking to the outside.

Figure 29:
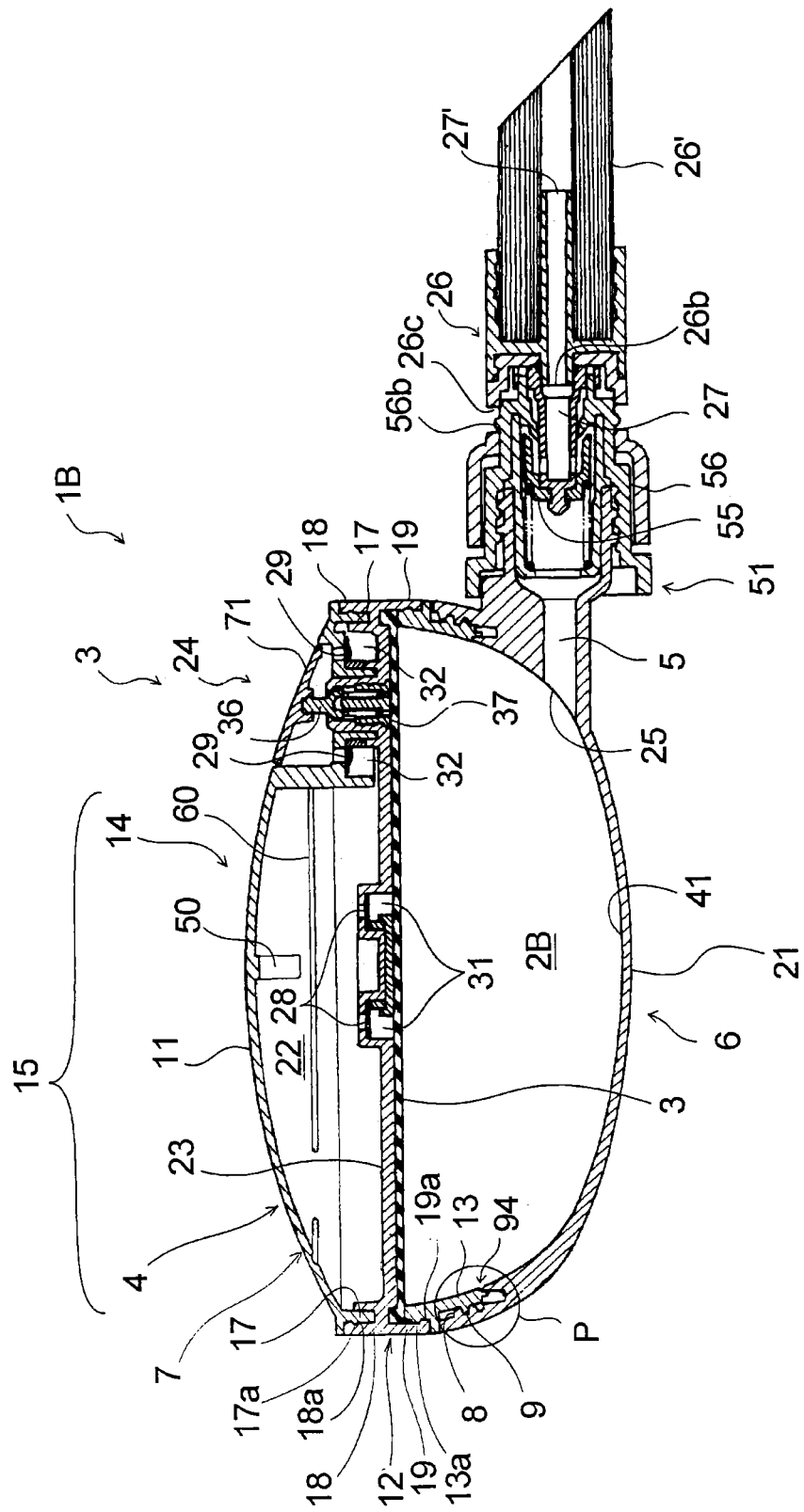
FIG. 29 is an enlarged sectional view at line V-V of FIG. 28.

As illustrated in FIG. 29, the container 1B according to the present embodiment includes the container body 6 which has a curved concave inner face and a cover body 7 which is attached to the container body 6 in a detachably attachable manner. The container body 6 includes a screwing convex stripe 8 at an inner circumferential face at an upper end part thereof. The cover body 7 includes a screwing convex stripe 9 at an outer circumferential face at a lower end part thereof. The container body 6 and the cover body 7 are screwed via the screwing convex stripe 8 and the screwing convex stripe 9 as being detachably attachable.

The cover body 7 includes a top face portion forming member 11, a partition wall forming member 12, a sheet-shaped elastic body 3 and an elastic body fixing member 13.

The top face portion forming member 11 forms a curved convex top face portion 14 which is convexed toward the outside of the container 1B. The whole or a part of the top face portion 14 forms a squeeze deformation portion 15 which is easily deformed by squeezing with a hand and is returned into an original state by releasing of the squeezing. The squeeze deformation portion 15 has a shape like a curved convex shape.

A cylindrical connection portion 17 is vertically arranged at a peripheral part of the top face portion forming member 11 in a direction opposite to a swelling direction of a curved convex face of the squeeze deformation portion 15. A pair of cylindrical connection portions 18, 19 extended vertically is arranged at a peripheral part of the partition wall forming member 12. The top face portion forming member 11 and the partition wall forming member 12 are integrated as being air-tightly connected by screwing the cylindrical connection portion 17 of the top face portion forming member 11 and the cylindrical connection portion 18 extended upwardly at the peripheral part of the partition wall forming member 12 via a screwing convex stripe 17a, and a screwing convex stripe 18a which are arranged respectively. Further, owing to the connection described above, a pressurization chamber 22 is formed between the top face portion forming member 11 and the partition wall forming member 12.

Figure 35:
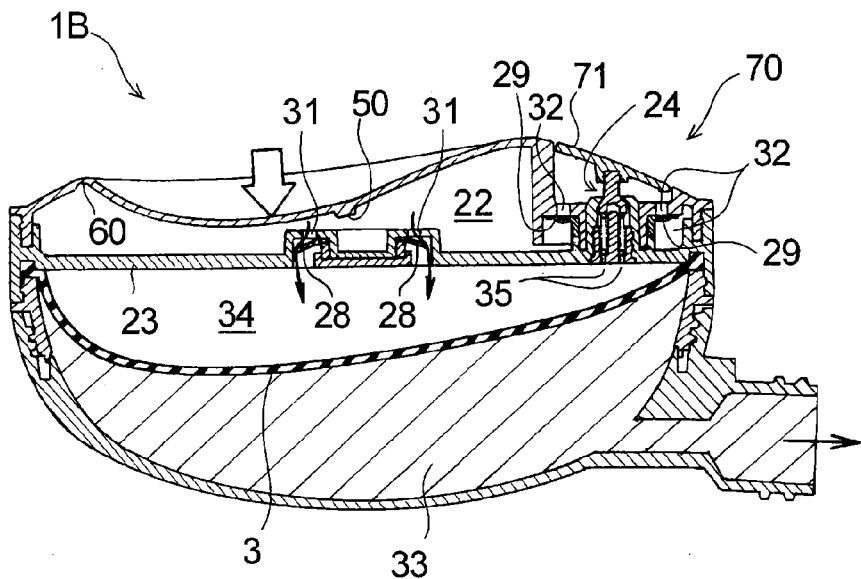
FIG. 35 is a sectional view illustrating a squeeze-deformed state of a squeeze deformation portion of the container of FIG. 28.

The partition wall forming member 12 forms a flat-plate-shaped partition wall 23 which is circular in plane view between the pressurization chamber 22 and the sheet-shaped elastic body 3. The partition wall 23 performs air-tight partitioning between the pressurization chamber 22 and the sheet-shaped elastic body 3. As illustrated in FIG. 35, there is substantially no deformation at the partition wall 23 even when the squeeze deformation portion 15 is deformed by being squeezed with a hand.

The sheet-shaped elastic body 3 is arranged along the partition wall 23 as being closed to the partition wall 23. In other words, one face of the partition wall 23 is covered with the elastic body 3. The sheet-shaped elastic body 3 is fixed as a peripheral part thereof being sandwiched at a space between the partition wall forming member 12 and the elastic body fixing member 13. The sheet-shaped elastic body 3 is not fixed to the partition wall forming member 12 other than the peripheral part. Accordingly, as illustrated in FIG. 35, the sheet-shaped elastic body 3 is swelled toward a curved concave inner face 41 of the liquid storage portion 2B with pressure (air pressure) of air fed by the pressurization means 4.

The partition wall forming member 12 and the elastic body fixing member 13 are integrated by screwing the elastic body fixing member 13 and the cylindrical connection portion 19 extended downwardly at the peripheral part of the partition wall forming member 12 via the screwing convex stripes 19a, 13a which are arranged respectively.

The elastic body fixing member 13 is cylindrical and an inner circumferential face thereof forms a curved concave face which is continued to the curved concave inner face of the container body 6. The curved concave inner face 41 of the liquid storage portion 2B is formed with the inner circumferential face of the elastic body fixing member 13 and the curved concave inner face of the container body 6. An opening portion 25 of a filling-delivering passage 5 at the liquid storage portion 2B side is opened into a circular or oval shape at a part of the curved concave inner face 41 of the liquid storage portion 2B, more specifically, at a part positioning right below an air-bleeding device 24 which is described later.

Figure 28:
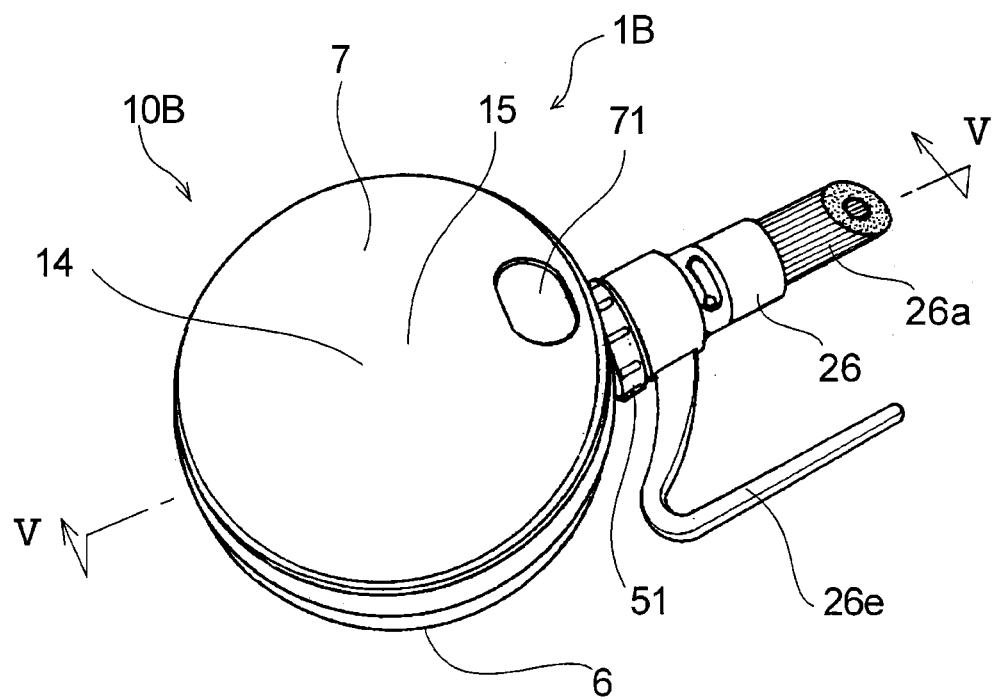
FIG. 28 is a perspective view illustrating a container according to an embodiment of the present inventions (seventh and eighth inventions).

As illustrated in FIG. 28, the container 1B includes a holding portion 10B which has the container body 6 and the cover body 7 and a filling-delivering portion 51 which protrudes from an outer circumferential section of the container body 6 and has a flow passage of fluid at the inside thereof. As illustrated in FIG. 28, the holding portion 10B roughly has a shape like a flat ellipsoidal body. The holding portion 10B is a section which is held by a user when delivering the content 33 of the container 1B. It is preferable for holding the holding portion 10B to sandwich the holding portion 10B with a thumb and other several fingers as putting the thumb on the top face portion 14.

Figure 30:
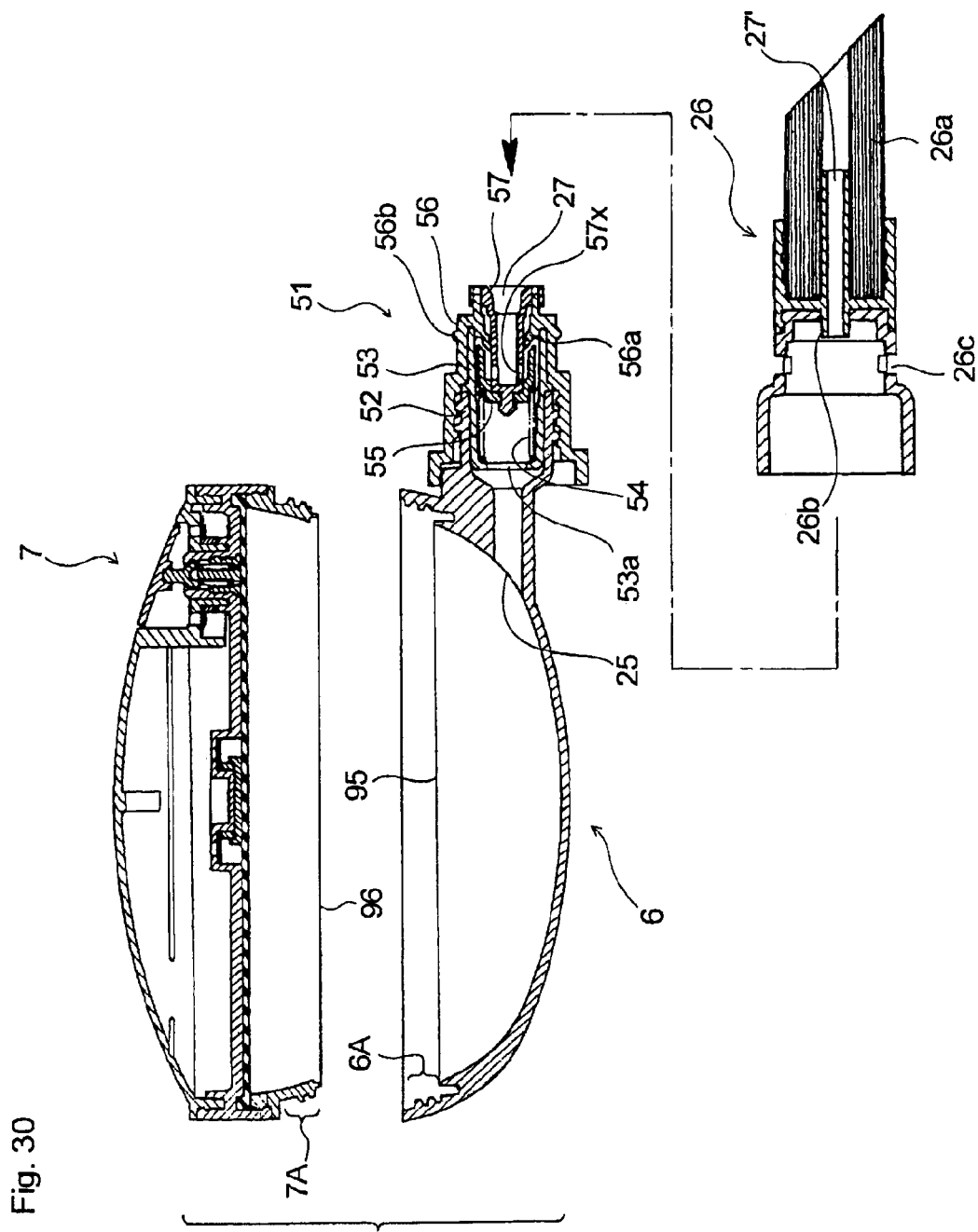
FIG. 30 is a view of the container of FIG. 28 (corresponding to FIG. 29) illustrating a state that a cover body and a container body are separated and a nozzle member for fluid applying is further detached.

As illustrated in FIG. 30, the filling-delivering portion 51 of the container 1B has the same structure as the filling-delivering portion 51 of the container 1 of the second embodiment.

In the filling-delivering portion 51, the valve member 55 is intimately contacted to the valve abutment portion 56a of the valve enclosure body 56 and the flow passage between the opening portion 25 and an opening portion 27 is closed in a state that the nozzle member 26 is not attached thereto, or in a state that a fluid filling nozzle of an aerosol container 90 or a pump-type container is not pressed thereto.

On the contrary, for attaching the nozzle member 26, the cylindrical connection portion 26b of the nozzle member 26 presses the nozzle connection member 57, and then, the nozzle connection member 57 and the valve member 55 coupled thereto are pressed toward the container body 6 side against urging force of a coil spring 54. Accordingly, the opening portion 25 and the opening portion 27 are in a communicated state and the delivery passage 5 for the content 33 is in an opened state from the opening portion 25 to an opening portion 27' for content delivery in the nozzle member. Here, a convex portion 56b arranged at an outer circumferential section of the valve enclosure body 56 and a groove or an opening portion 26c for locking arranged at the nozzle member 26 are engaged by twisting the nozzle member 26 after covering the valve enclosure body 56. Accordingly, the coupling state with the valve enclosure body 56 and the flow passage from the opening portion 25 to the opening portion 27' are stably maintained.

The nozzle member 26 is to be used for delivering the content 33 in the container 1B. When the liquid 33A, 33B is filled into the container 1B, the nozzle member 26 is detached from the filling-delivering portion 51 (more specifically, the valve enclosure body 56), as illustrated in FIG. 34.

Owing to replacement of the nozzle member 26, it is possible to change the passage from the opening portion 25 at the container body side to the opening portion 27' for content delivery in length or diameter. It is possible to be replaced with a nozzle member being different in dimensions of the opening portion 27' at the nozzle top end side, or the like. Further, it is also possible to replace a brush-equipped nozzle member having a brush 26a at a periphery thereof with a nozzle member without such a brush. The brush-equipped nozzle member 26 having the brush 26a is suitable for applying a hair care agent such as hair dye and hair treating agent, a skin care agent, or the like to hair, scalp, other skin, or the like. Here, a so-called partition hook 26e in FIG. 28 is used for parting hair.

Further, the delivery passage 5 may be formed by fixing the nozzle member 26 directly to a member which forms a bottom face portion 21 of the container body 6 in a permanently-set manner or a detachably attachable manner.

When filling the liquid 33A, 33B into the container 1B, the nozzle connection member 57 is pressed by a nozzle member 91 of a later-mentioned pump-type injector or an aerosol container, for example. In this case as well, the nozzle connection member 57 and the valve member 55 coupled thereto are pressed toward the container body 6 side. Accordingly, the opening portion 25 and the opening portion 27 which is to be a filling port are to be in a communicated state.

A preferable example of a method of filling a first agent and a second agent of two-agent type hair dye into the container 1B of the present embodiment will be described.

First, the second agent of the two-agent type hair dye is filled, as the fluid 33B, into the container 1B with a pump-type injector (not illustrated). As the pump-type injector, it is possible, for example, to use a pump type container which includes a nozzle member to be pressed to the abovementioned nozzle connection member 57 of the container 1B and which discharges a stored content as performing predetermined operation in a state that nozzle connection member 57 is pressed to the nozzle member. Examples of the predetermined operation to discharge a content include up-down movement or front-back movement of a lever and repetition of pressing of a pressing portion like a press button.

An amount of the liquid 33B filled into the liquid storage portion 2B of the container 1B as described above is measured by visually observing where a liquid level of the liquid 33B positions in the scale 98. Here, in a case without a scale, it is also possible only to acknowledge a rough amount.

Next, as illustrated in FIG. 34, the first agent of the two-agent type hair dye having higher viscosity than the second agent is filled, as the liquid 33A, into the container by the aerosol container 90 as the filling-delivering portion 51 of the container 1B is downwardly oriented. Specifically, the liquid 33A in the aerosol container 90 is filled into the liquid storage portion 2B of the container 1B by depressing the nozzle member 91 of the aerosol container 90 while the abovementioned nozzle connection member 57 of the container 1B is pressed to the nozzle member 91.

In a preferable embodiment of a method for filling liquid according to the present invention, filling of the liquid 33A with the aerosol container 90 is performed under conditions that the discharge passage 94 capable of discharging air 93 in the liquid storage portion 2B is arranged at the liquid storage portion 2B of the container 1B and that excessive increase of pressure in the liquid storage portion 2B is suppressed by the discharge passage 94 while filling the liquid 33A with the aerosol container 90.

When filling liquid having high viscosity, it is preferable to fill the liquid by using an aerosol container 90, in particular, an aerosol container having high gas pressure. In a case that the liquid 33A is filled from the aerosol container 90 into a container which is completely sealed except for the opening portion 27 which is to be a filling port, there may occur problems of breakage, burst or unscrewing of the container 1B. On the contrary, when filling of the liquid 33A is performed with an aerosol container under conditions that excessive increase of pressure in the liquid storage portion 2B is suppressed by the discharge passage 94, the above problems can be prevented.

However, in a case that a discharge passage having large sectional area is arranged as the discharge passage 94, a phenomenon that the liquid 33A is upraised as penetrating a liquid level of the previously-filled liquid 33B is more likely to occur when the liquid 33A having high viscosity is filled into the container 1B by the aerosol container.

When such a phenomenon occurs, it becomes difficult to check the filled amount of the liquid 33A while observing a liquid level of the liquid 33B or a liquid level of mixture of the liquid 33B and the liquid 33A. Consequently, the amount of the liquid 33B cannot be acknowledged by observing the liquid level.

Accordingly, in a preferable embodiment of a method for filling liquid according to the present invention, filling of the liquid 33A with the aerosol container 90 is performed under conditions that the discharge passage is arranged not to provide communication until relatively minute pressure or predetermined pressure and that a positive pressure state in the liquid storage portion 2B generated by filling of the liquid 33A with the aerosol container 90 continues until the filling of the liquid 33A is completed.

That is, filling of the liquid 33A is performed under conditions that the air 93 in the container 1B is compressed owing to filling of the liquid 33A when the liquid 33A is filled by the aerosol container 90 and predetermined pressure is applied to the liquid level or the liquid to be filled by the compressed air 93.

Consequently, it is possible to effectively suppress the phenomenon that the liquid 33A is upraised as penetrating a liquid level of the previously-filled liquid 33B.

The liquid storage portion 2B of the container 1B of the present embodiment is provided with the discharge passage 94 which enables to perform such filling. That is, when the liquid 33A is filled into the liquid storage portion 2B by the aerosol container as illustrated in FIG. 34, the discharge passage 94 capable of discharging the air 93 in the liquid storage portion 2B is arranged in the container 1B as illustrated in FIG. 33. The discharge passage 94 is formed to increase air pressure in the liquid storage portion 2B owing to filling of the liquid 33A with the aerosol container and to maintain the positive pressure state during filling the liquid. Further, the discharge passage 94 is formed so as not to leak the liquid 33A, 33B in the liquid storage portion 2B to the outside.

Figure 31:
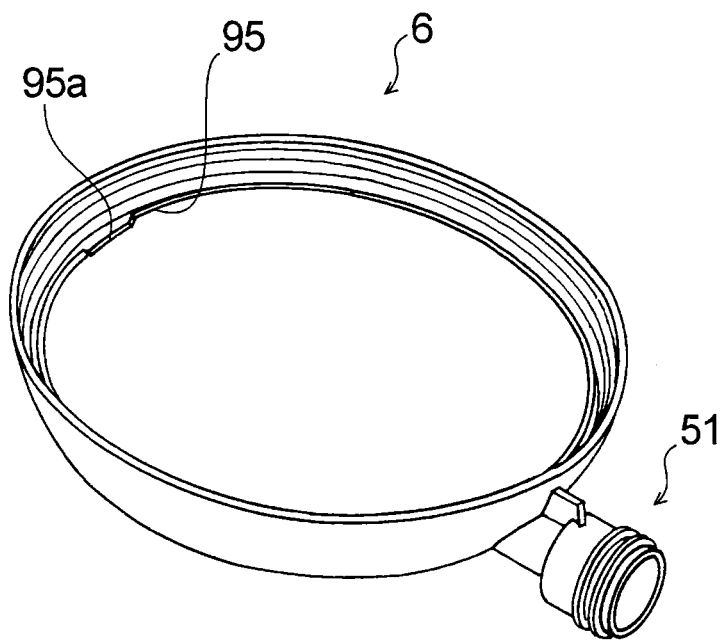
FIG. 31 is a perspective view illustrating a concave portion for forming a discharge passage formed at a circular seal portion of the container body.
Figure 32:
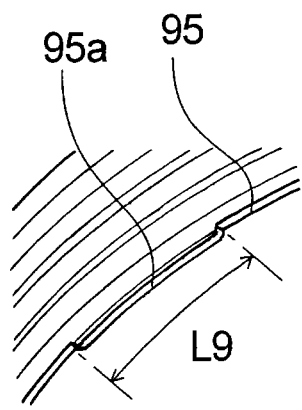
FIG. 32 is a partially enlarged view of FIG. 31.

The discharge passage 94 of the container 1B will be described more specifically. As illustrated in FIG. 33, circular seal portions 95, 96 to increase sealing tightness with intimate contact as screwing the container body 6 and the cover body 7 are formed respectively at the container body 6 and the cover body 7 in the container 1B. As illustrated in FIGS. 31 and 32, a concave portion 95a to form the discharge passage 94 is formed at a part in the circumferential direction of the circular seal portion 95 at the container body 6 side. The concave portion 95a forms a part of the discharge passage 94. That is, the existence of the concave portion 95a causes a gap between the circular seal portions 95, 96 or a section having a lower degree of tightness than other sections. The gap or the section structures a part of the discharge passage 94.

In the example illustrated in the drawings, the concave portion 95a to generate the discharge passage 94 is formed at an upper end part of the circular seal portion 95 at the container body 6 side. Instead of the above, it is also possible to form at an outer face side of the circular seal 95. Further, instead of the circular seal portion 95 at the container body 6 side, it is also possible to form at an upper end part or an inner face side of the circular seal portion 96 at the cover body 7 side.

Figure 37:
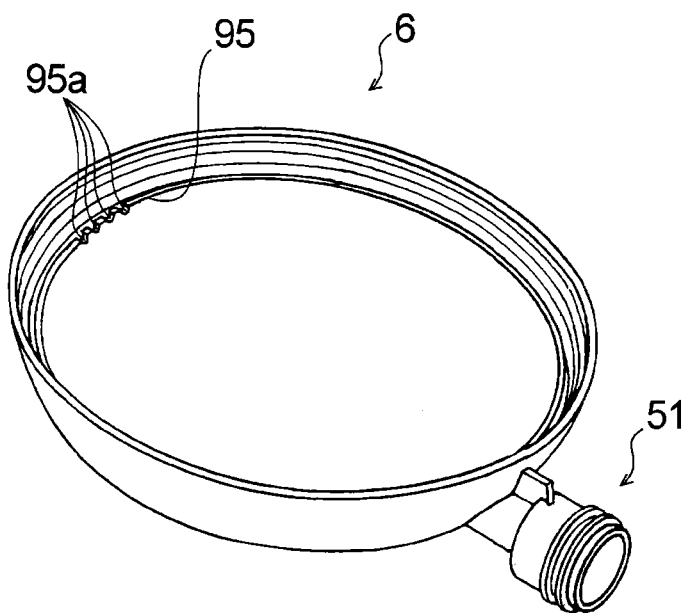
FIG. 37 is a view (corresponding to FIG. 31) illustrating another example of the concave portion for forming a discharge passage formed at the circular seal portion of the container body.

Further, with respect to the concave portion 95a to generate the discharge passage 94, only one or a plurality of the concave portion 95a may be formed in the circumferential direction of the container body 6. An example in which a plurality of concave portions 95a is formed is illustrated in FIG. 37.

Further, in the container 1B of the present embodiment, the discharge passage 94 provides communication between the inside of the liquid storage portion 2B and the outside of the container via a minute gap 99 which is formed between the container body 6 and the cover body 7 at a screwing part of the container body 6 and the cover body 7, as illustrated in FIG. 33. Accordingly, even if the liquid 33 leaks from the liquid storage portion 2B into the gap 99, the liquid 33 is prevented from directly leaking to the outside of the container 1B. In particular, in a case that the discharge passage 94 provides communication between the inside of the liquid storage portion 2B and the outside of the container via a minute space 97 between a face having a screwing convex stripe 8 at the container body 6 and a face having a screwing convex stripe 9 at the cove body 7, leaking of the liquid to the outside of the container 1B is prevented further reliably owing to existence of the screwing convex stripes 8, 9 which are spirally extended approximately along the circumferential direction.

Further, after usage of the container, the container body 6 and the cover body 7 can be separated and cleaned, so that liquid entered into the space 97 can be easily removed. It is preferable that the liquid storage portion has a depth which is smaller than a diameter of the liquid storage portion at a center part in the depth direction.

In the container 1B of the present embodiment, the liquid 33B and the liquid 33A which are filled sequentially to the inside thereof can be mixed by holding and shaking the container 1B with a hand.

Further, the container 1B of the present embodiment includes a squeeze deformation portion 15 which is deformed by squeezing with a hand and is returned into an original state by releasing the squeezing. The liquid 33 in the liquid storage portion 2B can be gradually delivered by repeating squeezing and releasing of the squeeze deformation portion 15.

More specifically, in the container 1B, a sheet-shaped elastic body 3 is arranged at the liquid storage portion 2B at the opposite part to the container body 6, as illustrated in FIG. 29. Then, the content 33 in the liquid storage portion 2B can be delivered to the outside via a flow passage from the opening portion 25 to the opening portion 27' at the nozzle member side by swelling the elastic body 3 toward the curved concave inner face 21 of the liquid storage portion 2B caused by pressure of gas as the pressurization means 4 feeding the gas toward the elastic body 3. In the container 1B of the present embodiment, the gas to swell the elastic body 3 is air (mixing gas including oxygen and nitrogen).

The pressurization means 4 in the container 1B of the present embodiment includes a first check valve 28 and a second check valve 29 as well as the squeeze deformation portion 15, the pressurization chamber 22 and the partition wall 23 which are described above.

Figure 36:
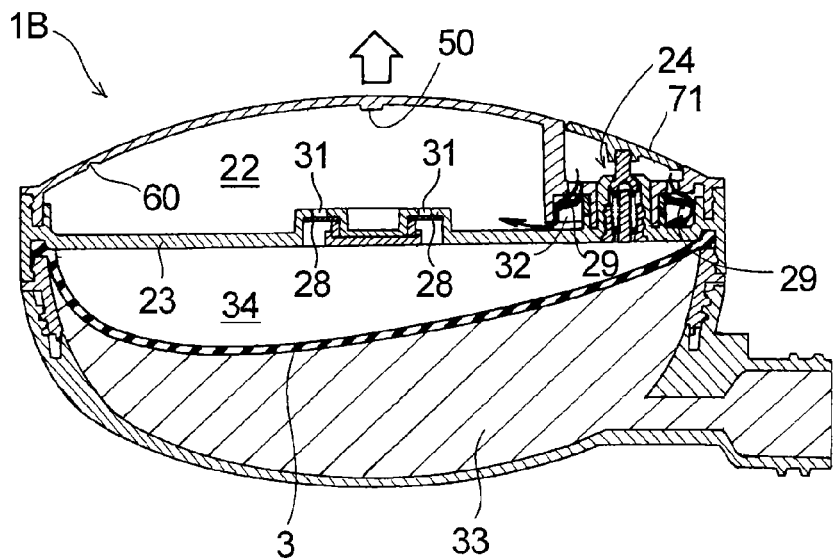
FIG. 36 is a sectional view illustrating a state that the squeeze deformation portion of the container of FIG. 28 is returned from a deformed state into an original state.

The first check valve 28 is arranged at a communication passage 31 which is formed at the partition wall 23 and feeds air in the pressurization chamber 22 toward the elastic body 3 as opening the communication passage 31 when the squeeze deformation portion 15 is deformed as being squeezed with a hand as illustrated in FIG. 35. On the other hand, when the squeezing of the squeeze deformation portion 15 is released as illustrated in FIG. 36, the communication passage 31 is closed by the first check valve 28 and the air swelling the elastic body 3 is prevented from being regurgitated to the pressurization chamber 22 accordingly.

The second check valve 29 is arranged at an intake passage 32 which is formed at the top face portion forming member 11 and closes the intake passage 32 when the squeeze deformation portion 15 is deformed as being squeezed with a hand as illustrated in FIG. 35. On the other hand, when the squeezing is released after squeezing the squeeze deformation portion 15 as illustrated in FIG. 36, the squeeze deformation portion 15 is returned into an original state owing to restoration characteristics thereof. Then, the second check valve 29 opens the intake passage 32 and air outside the container 1B inflows into the pressurization chamber 22.

The squeeze deformation portion 15 includes a reinforcement portion 50 being thicker than other sections and a thin-walled portion 60 being thinner than other sections. Owing to the above, the squeeze deformation portion 15 can be deformed with small force and restoration characteristics thereof from a deformed state into an original state are improved as well.

Further, the container 1B of the present embodiment includes the air-bleeding device 24 which discharges air accumulated in an inflation chamber 34 to the outside after delivering the content 33. The inflation chamber 34 of the present embodiment is a space between the partition wall 23 and the elastic body 3. In an initial state before squeezing the squeeze deformation portion 15, there does not exist a space being anything like a chamber between the partition wall 23 and the sheet-shaped elastic body 3 as the both being intimately contacted. However, the inflation chamber in the present application includes this space between the partition wall 23 and the sheet-shaped elastic body 3 which are in an intimately contacted state. Here, it is also possible that a gap or a space having predetermined volume exists between the partition wall 23 and the elastic body 3 from the initial state before squeezing the squeeze deformation portion 15.

The air-bleeding device 24 includes a plug member 36 which is urged by a coil spring 37 (elastic member), and normally, closes the communication passage 35 which connects the outside of the container and the inflation chamber 34 between the partition wall 23 and the elastic body 3. Then communication passage 35 is opened by pressing a button member 71 which is coupled to the plug member 36.

According to the container 1B of the present embodiment, the sheet-shaped elastic body 3 can be gradually swelled to the curved concave inner face 41 side of the liquid storage portion 2 by repeating squeezing of the squeeze deformation portion 15 and releasing thereof in a state that the content 33 which is liquid or gel is filled into the liquid storage portion 2B. Accordingly, an amount or speed of delivering the content can be arbitrarily controlled by appropriately controlling an amount or speed of swelling the elastic body 3.

Further, being different from the container of Patent Literature 1, since the content 33 is squeezed and delivered by the elastic body 3, it is possible to stably deliver an appropriate amount of content even when the content 33 becomes less. Here, in the container 1B of the present embodiment, the sheet-shaped elastic body 3 which has been plane-shaped at the beginning can be swelled until becoming to be a solid shape (solid shape being like a slightly irregular hemisphere) along the shape of the curved concave inner face 41 of the liquid storage portion 2B.

The liquid (first agent) to be filled by an aerosol container has viscosity preferable being in a range between 10000 mPa·s and 200000 mPa·s. Further, the second liquid (second agent or the like) which is filled before filling of the liquid to be filled by an aerosol container has viscosity preferably in a range between 50 mPa·s and 5000 mPa·s being lower than that of the liquid to be filled by an aerosol container.

Not limited to the abovementioned embodiments, the seventh and eighth inventions may be appropriately modified.

For example, other liquid may not be filled into the liquid storage portion 2B of the container 1B before filling of the liquid to be filled by an aerosol container. Further, the discharge passage 94 may be arranged at another section in the circumferential direction of the container body 6. Further, instead of that the whole container body 6 is formed of transparent plastic, it is possible that only a part of the container may be set to be transparent so that a liquid level is visible through the part. Further, other than a combination of numerals and lines, the scale may be formed of only lines or only numerals. Furthermore, the scale may be eliminated.

Material of respective components of the squeeze containers 1, 1', 1A, 10 and the container 1B will be described.

For example, polyolefin-based thermoplastic resin such as polypropylene, thermoplastic elastomer, or the like may be used as forming material of the squeeze deformation portion 15. Here, from a viewpoint of being easily deformed by squeezing with a hand and a viewpoint of natural returning into an original state by releasing of the squeezing, it is preferable to use polypropylene. Examples of the thermoplastic elastomer include styrene-based elastomer, polyolefin-based elastomer, polyester-based elastomer, and polyamide-based elastomer.

Further, from a viewpoint of natural returning into an original state after being deformed, it is preferable that the squeeze deformation portion 15 is shaped like a curved convex face having an arc sectional shape of which curvature radius is in a range between 50 mm and 100 mm.

Further, examples of forming material of the elastic body 3 include rubber such as ethylene-propylene-diene rubber (EPDM), silicone rubber and natural rubber and gel such as urethane. From viewpoints of durability and a content-resistant strain, it is preferable that forming material of the elastic body 3 is EPDM.

The third embodiment may adopt a sheet or a thin plate made of synthetic resin, a rubber-made sheet, a metal-made thin plate or the like as forming material of the flexible member 8. However, it is not limited to the above.

Further, in each embodiment, it is preferable that forming material of the partition wall forming member 12, the elastic body fixing member 13 and the container body 6 is synthetic resin such as thermoplastic resin and thermoset resin. However, it is not limited to the above. Further, it is also possible that a part of each member is formed of metal or other material.

Not limited to the abovementioned embodiments, the present (first to eighth) inventions may be appropriately modified.

Here, it is also possible to eliminate either or both of the reinforcement portion 50 and the thin-walled portion 60 of the squeeze deformation portion 15. Further, a bellows-shaped pump mechanism may be arranged at the top face portion 14 as the pressurization means. Further, a variety of well-known check valves may be used as the first check valve and/or the second check valve. For example, it is possible to use a swing-type check valve, a ball-type check valve, a spring-disc-type check valve and the like.

Further, in the abovementioned containers of each embodiment, the gas to swell the elastic body is air (mixing gas including oxygen and nitrogen). However, the gas in the present invention may be gas other than air.

INDUSTRIAL APPLICABILITY

According to the squeeze container of the present invention (first invention), it is possible to stably deliver an appropriate amount of a content even when a remaining amount of the content becomes less.

According to the present invention (second invention), the squeeze container is superior in deformability due to squeezing and in restoration characteristics from a deformed state and content delivering operation can be performed smoothly.

According to the squeeze container of the present invention (third invention), squeezing operation to deliver a content can be performed in a wide range as providing high operability.

According to the present invention (fourth invention), the intake-discharge integrated valve device is compact, while a plurality of intake holes having a check valve and a discharge passage can be closely arranged.

According to the squeeze container of the present inventions (fifth and sixth inventions), delivery of a content is stopped relatively rapidly when squeezing of a squeeze deformation portion is released and a user can easily perform delivering of the content and stopping of the delivering without causing a feeling of strangeness.

According to the method of filling liquid of the present invention (seventh invention), an amount of liquid can be easily seen even in a case that liquid having high viscosity is filled by an aerosol container.

Further, according to the container of the present invention (eighth invention), liquid is more unlikely to be upraised like a mountain-shape even when liquid having high viscosity is filled to the inside by an aerosol container and an amount of the liquid filled to the inside can be acknowledged relatively accurately with visual observation.

The invention claimed is:

1. A squeeze container, comprising:
a concave storage portion in which a content is stored;
a sheet-shaped elastic body which is arranged to cover an opening portion of the storage portion;
a pressurizer which swells the elastic body to a storage portion side with gas pressure; and
a delivery passage which provides communication between the inside and outside of the storage portion and which delivers the content squeezed by the elastic body to the outside,
a solid shape of an inner face of the storage portion being formed to be matched with a solid shape of the elastic body when the elastic body is swelled to be a predetermined size,
wherein the pressurizer is structured to be capable of gradually swelling the elastic body by repeating squeezing with a hand and releasing of the squeezing.

2. The squeeze container according to claim 1,
wherein the storage portion includes the opening portion, is approximately circular, and has a curved, concave bottom face, and
a depth of the storage portion is smaller than a diameter of the storage portion at a center part in a depth direction.

3. The squeeze container according to claim 1,
wherein the pressurizer includes:
a squeeze deformation portion having a curved convex face, which is deformed by squeezing with a hand, and which is returned to an original state by releasing of the squeezing,
a flat-plate-shaped partition wall arranged between the squeeze deformation portion and the elastic body,
a pressurization chamber of which inner volume is decreased with deformation of the squeeze deformation portion as being arranged between the squeeze deformation portion and the partition wall,
a first check valve which opens a communication passage to feed air in the pressurization chamber to a space between the elastic body and the partition wall when the squeeze deformation portion is squeezed, and
a second check valve which opens an intake passage to suck outer air into the pressurization chamber when squeezing of the squeeze deformation portion is released.

4. The squeeze container according to claim 3,
wherein the first check valve is arranged at the partition wall.

5. A squeeze container, comprising:
a concave storage portion in which a content is stored;
a sheet-shaped elastic body which is arranged on the storage portion;
a pressurizer which swells the elastic body to a storage portion side with gas pressure; and
a delivery passage which provides communication between the inside and outside of the storage portion and which delivers the content squeezed by the elastic body to the outside,
wherein the pressurizer includes a squeeze deformation portion which is deformed by squeezing with a hand and which is returned into an original state by releasing of the squeezing and is structured to be capable of swelling the elastic body by squeezing and deforming the squeeze deformation portion, and
the squeeze deformation portion has a curved convex face toward the outside of the container and includes a linear reinforcement portion which traverses an apex portion of the squeeze deformation portion, and a linear thin-walled portion which is formed in a direction along a circumferential edge of the squeeze deformation portion.

6. The squeeze container according to claim 5,
wherein the pressurizer is structured to be capable of gradually swelling the elastic body by repeating squeezing and releasing of the squeeze deformation portion.

7. The squeeze container according to claim 5,
wherein the thin-walled portion is formed of discontinuous lines.

8. A squeeze container, comprising:
a concave storage portion in which a content is stored,
a sheet-shaped elastic body arranged on the storage portion,
a pressurizer which swells the elastic body to a storage portion side with air pressure, and
a delivery passage which provides communication between the inside and outside of the storage portion and which delivers the content squeezed by the elastic body to the outside,
wherein the pressurizer includes a squeeze deformation portion which is deformed by squeezing with a hand and which is returned into an original state by releasing of the squeezing, and a check valve which opens an intake passage to suck outer air when the squeezing is released, and is structured to be capable of gradually swelling the elastic body by feeding air into an inflation chamber of which part is structured by the elastic body by repeating squeezing and releasing of the squeeze deformation portion,
an air-bleeding device which discharges air in the inflation chamber to the outside is provided to the container,
the air-bleeding device includes an elastic member, a plug member and a communication passage which provides communication between the inflation chamber and the outside of the container via a storage portion of the elastic member,
the plug member closes the communication passage as being urged by the elastic member and opens the communication passage when the plug member is pressurized, and
the intake passage which is opened and closed by the check valve surrounds a periphery of the air-bleeding device.

9. The squeeze container according to claim 8,
wherein the air-bleeding device includes a button member which is formed continuously to the plug member, and
the plug member opens the communication passage against urging of the elastic member by squeezing the button member with the hand.

10. The squeeze container according to claim 9,
wherein the button member covers an upper side of the intake passage.

11. A squeeze container, comprising:
a storage portion in which a content is stored, the storage portion having a delivery passage which provides communication between the inside and outside of the storage portion, an inflation chamber, and
a pressurizer,
wherein volume of the inflation chamber is increased owing to that the pressurizer fills gas into the inflation chamber and the content in the storage portion is delivered to the outside of the storage portion via the delivery passage owing to increase of the volume of the inflation chamber,
at least a part of the inflation chamber is structured with an elastic body and the volume of the inflation chamber is increased with deformation of the elastic body while gas is filled into the inflation chamber by the pressurizer,
an inflation absorbing portion which decreases the volume of the inflation chamber at the time when gas-filling into the inflation chamber by the pressurizer is completed,
the storage portion is concave and has an opening at an upper face,
the inflation chamber is structured with a partition wall and the elastic body which is arranged to cover an entirety of the opening,
the pressurizer includes a pressurization chamber which is structured with the partition wall and a squeeze deformation portion, a first check valve which allows only ventilation toward the inflation chamber from the pressurization chamber, and a second check valve which allows only inflow of outer air into the pressurization chamber, and
the inflation absorbing portion includes a displacement portion, formed at the partition wall, which is displaced toward a side opposite to the elastic body when squeezing of the squeeze deformation portion is released.

12. The squeeze container according to claim 11,
wherein the displacement portion is a flexible portion having at least a center part to be displaced toward the pressurization chamber when squeezing of the squeeze deformation portion is released.

13. The squeeze container according to claim 12,
wherein the flexible portion is deformed to be convex toward the elastic body side during squeezing of the squeeze deformation portion and is deformed to be convex toward the pressurization chamber side when the squeezing is released.

14. The squeeze container according to claim 11,
wherein the displacement portion is moved toward the elastic body when squeezing of the squeeze deformation portion is applied and is moved toward a side opposite to the elastic body when the squeezing is released.

15. A method of filling liquid to fill liquid discharged from an aerosol container into a container which comprises a liquid storage portion with which an amount of filled liquid is visible from the outside, comprising performing to fill liquid with the aerosol container under conditions that a minute discharge passage capable of discharging air in the liquid storage portion is arranged at the liquid storage portion and that a positive pressure state in the liquid storage portion generated by the filling of the liquid continues until the filling is completed while excessive increase of pressure in the liquid storage portion is suppressed by the discharge passage.

16. The method of filling liquid according to claim 15,
wherein the liquid to be filled by the aerosol container is a first agent containing an alkaline agent of two-agent type hair dye and the second liquid is a second agent containing hydrogen peroxide of the two-agent type hair dye.

17. A container adapted to be filled with liquid by an aerosol container, comprising a liquid storage portion with which an amount of the filled liquid is visible from the outside,
wherein a discharge passage capable of discharging air in the liquid storage portion at the time of filling liquid is arranged at the liquid storage portion,
the discharge passage is formed to increase air pressure in the liquid storage portion owing to filling of the liquid and to maintain a positive pressure state during filling of the liquid while preventing the liquid in the liquid storage portion from leaking to the outside,
the liquid storage portion is formed by screwing a container body and a cover body, and
the discharge passage provides communication between the inside of the liquid storage portion and the outside of the container via a minute gap which is formed between the container body and the cover body by the screwing.

* * * * *